US006294174B1

(12) United States Patent
Krsmanovic et al.

(10) Patent No.: US 6,294,174 B1
(45) Date of Patent: Sep. 25, 2001

(54) PEPTIDES IMMUNOLOGICALLY RELATED TO KNOWN VIRAL PROTEIN

(75) Inventors: Velibor Krsmanovic, Lyons (FR); Irena Cosic, Victoria (AU); Jean-Michel Biquard, Palaiseau (FR); Milton T. W. Hearn, Victoria (AU)

(73) Assignees: Monash University, Victoria (AU); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 08/290,736

(22) PCT Filed: Feb. 19, 1993

(86) PCT No.: PCT/FR93/00171

§ 371 Date: Nov. 16, 1994

§ 102(e) Date: Nov. 16, 1994

(87) PCT Pub. No.: WO93/17108

PCT Pub. Date: Sep. 2, 1993

(30) Foreign Application Priority Data

Feb. 19, 1992 (FR) .................................... 92 01883

(51) Int. Cl.$^7$ .................................... A61K 39/21
(52) U.S. Cl. .................................... 424/188.1; 424/208.1; 530/324; 530/326; 435/5
(58) Field of Search .................................... 530/350, 333, 530/324–326; 424/184.1, 185.1, 186.1, 187.1, 188.1

(56) References Cited

FOREIGN PATENT DOCUMENTS 0 431 189   6/1991  (EP) .
91/04543    4/1991  (WO) .

OTHER PUBLICATIONS

Barbucci et al, "Antigen–Antibody Recognition by Fourier Transform IR Spectroscopy/Attenuated Total Reflection Studies: Biotin–Avidin Complex as an Example", Biopolymers 31:827–834 (1991).
Cosic et al, "Prediction of <hot spots> in interleukin–2 based on informational spectrum characteristics of growth–regulating factors. Comparison with experimental data", Biochimie 71(3):333–342 (1989).
Cosic et al, "Resonate recognition model and protein topography: Model studies with myoglobin, hemoglobin and lysozyme", European Journal of Biochemistry 198(1):113–119 (1991).
Wildner et al., 1997, "Database screening for molecular mimicry", Immunol. Today 18:252.*
Baum et al., 1997, "Also", Immunol. Today 18:252–253.*
Geysen et al., 1988, "Cognitive features of continuous antigenic determinants", J. Molec. Recog. 1:33–41.*
Boehncke et al., 1993, "The importance of dominant negative effects of amino acid side chain substitution in peptide–MHC molecule interactions and T cell recognition", J. Immunol. 150:331–341.*
Murphy, F., 1996, "Virus taxonomy", in *Fields Virology*, Third Edition, Fields et al., eds., Lippincott–Raven Publishers, Philadelphia, pp. 51–54.*
Birch, S., et al., 1995, "Preliminary expansion of the resonant recognition model to incorporate multivariable analysis", Austral. Phys. Eng. Science Med. 18(4):197–207.*
Abaza, M.–S. and M. Z. Atassi, 1992, "Effects of amino acid substitutions outside an antigenic site on protein binding to monoclonal antibodies of predetermined specificity obtained by peptide immunization: demonstration with region 145–151 (antigenic site 5) of myoglobin", J. Prot. Chem. 11(6):687–698.*
Burrows, S. R., et al., 1992, "The specificity of recognition of a cytotoxic T lymphocyte epitope", Eur. J. Immunol. 22:191–195.*
Mouritsen, S., et al., 1994, "Attachment of oligosaccharides to peptide antigen profoundly affects binding to major histocompatibility complex class II molecules and peptide immunogenicity", Eur. J. Immunol. 24:1066–1072.*
Geysen, H. M., et al., 1988, "Cognitive features of continuous antigenic determinants", J. Molec. Recog. 1(1):32–41.*

* cited by examiner

*Primary Examiner*—Laurie Scheiner
*Assistant Examiner*—Jeffrey S. Parkin
(74) *Attorney, Agent, or Firm*—Nixon & Vanderhye P.C.

(57) ABSTRACT

Peptides immunologically related to proteins expressed by a viral agent, having a sequence of amino acids ordered by means of the protein informational analysis techniques using the Fourier transform method with reference to the amino acid sequence of a target antigen against which antibodies are desired to be formed, or lymphocytes desired to be directed. The sequence has in the Fourier spectrum, one or more frequencies of practically the same value as the frequency of frequencies characteristic of the target antigen.

6 Claims, 18 Drawing Sheets

PEPTIDES IMMUNOLOGICALLY RELATED TO KNOWN VIRAL PROTEIN

The invention relates to peptides immunologically related to proteins of a viral agents, that is to say, constituting, with regard to their immunological properties, analogues of proteins involved in a viral pathology or of antibodies formed against these proteins.

It is also concerned with the biological applications of these peptides, in particular for diagnostic, preventive and therapeutic aims.

It is known that the immunological approach is mainly used to treat or establish a diagnostic of human or animal pathologies in which infectious agents or also cellular or extra cellular constituents of the organism responsible for autoimmunity are involved.

The expression "infectious agent" as used in the description and claims, refers to viral pathogenic agents, this term covering retroviral agents or also cells infected by said agents.

This immunological approach relies upon the use of antibodies capable of recognising specifically the infectious antigen, or on the induction of immune responses of the organism, including also the auto-antibodies.

Generally, antibodies are produced by immunisation of animals against the infectious agent, previously inactivated, or against proteins purified from this agent.

However, this process is often expensive and requires the use of sophisticated techniques for the production and isolation of the infectious agents, as well as for the purification of proteins.

Furthermore, in the case of particularly virulent agents, these procedures require laboratory logistics which must follow very strict security rules, which make the procedures even more expensive.

To be useful in therapeutic, it is assumed that the antibodies must have a neutralising effect in vivo vis-a-vis the infectious agent.

However, in many pathological situations, the circulating or induced antibodies do not have such an effect on the antigenic proteins.

This problem is particularly crucial in the case of the pathologie(s) induced by the virus HIV in humans, usually called AIDS (acquired immune deficiency syndrome). The different clinical stages of the infection by HIV are indeed followed by important changes in the immune system resulting from the extreme affinity of the virus for the receptor CD4 of T4 lymphocytes, leading to the death of infected cells. Furthermore, other types of cells are infected by HIV.

It should be reminded that HIV generally refers to the retroviruses of type HIV-1 and HIV-2, isolated nowadays from the human, and the retroviruses type SIV isolated from the monkey, which are different from HIV-1 and HIV-2, as well as their numerous variants.

Studies involving the production of vaccines against HIV are mainly aimed at using viral antigens or their fragments obtained from proteins of HIV. Interest has focussed mainly on the glycoprotein of the envelope of the virus coded by the gene ENV, gp160 (gp120/41) or a fragment thereof. More recently, experimental vaccination has been approached by using internal constituents of the virus such as the proteins coded by the gene GAG (and POL).

Various animal models are used in those trials, including primates.

A certain protective effect against infection by HIV has been observed in the case of monkeys inoculated with this virus. However, these results have to be considered with caution considering the fact that these animals cannot develop AIDS.

Experimental vaccination in humans are currently on trial, mainly with the proteins or the peptides deriving from the gene ENV.

However, the efficacy of such vaccines is far from being established, and the development of a vaccine against AIDS raises numerous problems. For example, the major problem resides in the fact that in seropositive subjects, as well as in patients, most of the circulating antibodies are not capable of neutralizing the viruses and/or of eliminating the cells carrying the virus in the patients' body. Even though certain circulating antibodies are neutralising agents in vitro, their protective effect in the organism has not been efficient.

Another immunological approach consists in generating the internal image of the antigen, i.e. the anti-idiotype antibody, then to utilise this new structure as an immunisation agent, rather than the antigen itself (see (1) and (2) in the references given at the end of the description).

Such an immunisation via the internal image of the antigen requires various stages.

First of all, one has to induce immunisation with the antigen, which will allow the production of antibodies AC1, or idiotypic antibodies, directed against this antigen.

Then, one has to immunize with idiotypic antibody AC1 in order to induce anti-idiotypic antibodies AC2, which carry the internal image of the initial antigen. This internal image of the antigen corresponds to the region of binding of this antigen with the antibody AC1.

Finally, immunisation with the anti-idiotype AC2 allows the production of the anti-anti-idiotypic antibodies AC3. These antibodies AC3 are capable of reacting with the initial antigen (1, 2). Furthermore, the anti-idiotype AC2 can activate the lymphocytes which would then be able to recognise the initial antigen, as in the case of direct activation of these cells by the antigen.

The induction of anti-idiotype AC2 can also be obtained against the receptors of sensitised T cells, which are responsible for the cellular immunity. It is indeed possible to generate at the same time T lymphocytes of which the receptors are capable of recognising the foreign determinants expressed at the surface of a virus or of infected cells, and the cellular determinants of type MHC (major hystocompatibility complex). This case thus refers to sensitised lymphocytes.

During this first step, the R1 receptors of these lymphocytes express structures corresponding to the idiotype, having in fact a function similar to that of the antibody AC1.

Immunisation by thus sensitised lymphocytes (or their membrane receptor R1) then allows the production of both anti-idiotypic antibodies AC2, as well as lymphocytes with receptors R2, similar to the antibodies AC2, and directed against, or recognising, the domain of the R1 lymphocyte receptor involved in the binding to the antigen. Finally, the R2 lymphocyte receptors or the AC2 anti-idiotypic antibodies, are capable of inducing a new response of lymphocyte cells, of which the R3 receptors recognise the initial antigen (1).

This use of the internal image of the antigen is particularly interesting in influencing the mechanism of lymphocyte sensitisation. The major advantage which results therefrom resides in the fact that, recognition of the antigen by sensitised lymphocytes with the internal image does not depend upon the genetic nature of the immunised host, because the restricted control of the identity of CMH of infected target cells, or of the virus does not represent any obstacle any more to their destruction (2).

In conclusion, the antibodies directed against the anti-idiotype, being able to crossreact with the initial antigen, are capable of inducing immunity in which B lymphocytes, as well as T lymphocytes, are involved.

However, the use of antibodies or anti-idiotypic lymphocyte receptors as vectors of the internal image of the antigen in the prevention or treatment of immuno deficient diseases, is not without danger.

Indeed, one has to be particularly careful when treatments involving the injection of anti-idiotypes in the organism are used (2). For example, in the guinea pig, the presence of certain fractions of anti-idiotypic antibodies (AC2), such as the sub-class IgG2, which are capable of fixing the complement, exerts a rather suppressive effect on the production of anti-anti-idiotypic (AC3) antibodies by IgG1, which do not fix the complement, both sub-classes of IgGs being present in the same serum. Besides the inconvenience related to 2 the immuno-suppressive effect of AC2 antibodies, very weak doses of antibodies (in the order of 10 ng in the mouse) must be administered, and this subcutaneously, and not intravenously, in order to avoid immunological perturbations.

As the classical immunological approach to problems of vaccination and therapeutic are not satisfactory, the inventors have searched for a different way to obtain immunological molecules, based on a physico-mathematical treatment of the amino acid sequence of an antigen.

Studies based on the technique of information analysis of proteins, in short IAP (known as "Resonant Recognition Model" RRM), using the method of Fourier transformation (in short MFT), particularly using the "Fast Fourier Transform" (in short FFT), has indeed shown that a group of proteins interacting with the same receptors, expresses a frequency or a period common to this group as well as to the receptor.

Any reference in the description which follows and the claims to the Fourier transformation and Fourier Spectra, covers FFT and FFT spectra.

This IAP technique, as particularly described in reference (3), is based on a model of the primary structure of a protein using a sequence of numbers, by assigning to each amino acid a defined parameter describing a physico-chemical property involved in the biological activity of the protein.

The best relationships have been obtained using parameters related to the energy of delocalised electrons of each amino acid. This energy can be calculated according to various physico-chemical parameters, characteristic of the amino acids, such as the pseudo-potential electron-ion interaction (PEII) of the delocalised electrons (4, 5).

By applying to these values the Fourier transformation, it is possible to obtain spectra carrying the same information as the original numeric sequence (6).

This theoretical approach has revealed itself to be of great interest in analysing the correlation existing between the energy distribution of the delocalised electrons along the primary structure of a macromolecule, and its biological and biorecognition functions.

Therefore, using such a technique it has been shown, by comparing several hundreds of proteins, that the different frequencies in the Fourier spectra could be related to their different biological functions, and that the sequences involved in the same biological function present the same periodic characteristics.

By multiplying the Fourier spectra of proteins having a same biological function, one can observe one or several common periodic elements or one or several common frequencies, characteristic of that biological activity, as seen by one or several peaks.

Such a frequency has been detected, for example, in peptide hormones and their receptors.

The use by the inventors of this theoretical approach to search for new molecules, foreign to the human or animal organism, but susceptible to induce antibodies which recognise viral antigens, has shown that the characteristic or major periodic elements, which are common to several proteins, can be used as a basis for the production of peptides immunologically active vis-a-vis said recognition reaction.

It is then an object of the invention to produce such peptides, namely analogues of proteins of viral agents, or analogues of antibodies formed against these proteins, i.e. capable of mimicking proteins and antibodies in terms of immunogenicity.

In particular it is an object to prepare peptides which are analogues of internal images of proteins, antigenic to these agents, corresponding or including the binding site with the antibody.

It is also an object of the invention to provide a procedure to obtain these peptides in order to elaborate a peptide sequence according to the desired immunogenicity with regards to the target antigen and to easily obtain the peptide by synthesis.

The invention also aims at the biological applications of these peptides, in particular to their use in diagnostic, preventive and therapeutic aids. Furthermore, the invention namely allows possibilities of treatment of auto-immunity by producing peptides capable of inducing antibodies, or lymphocytes capable of recognising autoimmune antibodies and, by destroying them, autoimmune lymphocytes.

The peptides, according to the invention, which are immunologically related to proteins of a viral agent, are characterised by the fact that they comprise or consist of a sequence of amino acids.

- as determined by the IAP numeric technique with regards to the amino acid sequence of a target antigen against which one wishes to produce antibodies or direct lymphocytes.
- different from the sequence of the protein(s) of the viral agent.
- presenting, in the Fourier spectrum, one or several frequencies practically of similar value to the frequency (frequencies) characteristic of the target antigen.

It should be stressed that the peptides determined by the IAP technique are artificial peptides, the sequences of which have been established on the basis of that of a target antigen and in such a way as to present in common with that antigen, one or several characteristic frequency (frequencies) of a given biological activity.

The expression "target antigen" refers as well to the protein expressed by the viral agent, or a fragment of that protein, as to an antibody produced against that protein or a fragment of that protein, or also to the antigen to be protected in the case of an autoimmune pathology, or still to a peptide whose amino acid sequence has been in its turn determined by the IAP numeric method.

The expression "characteristic frequency" relates to the major or dominant frequency (frequencies) in the Fourier spectra analysed, which appear(s) to be linked to the immunoreactivity with the target antigen or the antigen to protect, (in opposite phase) and carries (carry) the pertinent information in terms of the antigenicity properties.

The reference to common frequencies, such as used in the description and the claims, means that the frequencies of the sequences studied have a same or similar value(s).

The invention aims in particular at a group of peptides of which the frequency (frequencies) in the Fourier spectrum is (are) in inversed phase to that of the characteristic frequency (frequencies) of the target antigen.

The invention also aims at another group of peptides of which the frequency (frequencies) in the Fourier spectrum is (are) in phase with the characteristic frequency (frequencies) of the target antigen.

One should notice that the peptides of a same family present, between them same frequency (frequencies) and same phase. On the other hand, their protein sequences are different, as well from each other as in relation to those of the target antigens.

The target antigen can be made of a viral protein or a fragment of such a protein having at least one antigenic site.

A group A of peptides such as determined with regards to that viral protein is characterised by the fact that the so called peptides present in the Fourier spectrum, in common with the viral protein, the characteristic frequency (frequencies) of that protein, but in inverse phase, and that they are able to induce antibodies which crossreact with the members of the same group.

These antibodies appear then able to recognise, by using, such as disclosed particularly in the examples, Elisa or Western Blot techniques, peptide structures different to those against which they have been formed, but which share with them spectral characteristics.

Inversely, a given peptide structure of a family of peptides is capable of giving a complex of the type antigen-antibody with the antibodies formed against other peptides of the family.

One should notice that the antibodies induced by the peptides of group A are analogues of the internal image of the viral protein, more precisely of the domain of this protein involved in the reaction of the type antigen-antibody.

The expression "analogues of the internal image of a protein" such as used in the description and the claims refers to the data obtained by the IAP method used as modelling means according to the invention.

In another aspect of the invention, the target antigen, in relation to which a peptide sequence is determined, is made of peptides of group A.

A group B of peptides, as determined with regards to peptides of group A is characterised by the fact that said peptides present, in their Fourier spectrum, one or several frequencies common to those characteristics of peptides A, in inverse phase with regards to the one or those of peptides A, but in phase with that (those) of the target antigen for which the peptides of group A have been determined.

One should notice that the peptides of group B are analogues of the internal image of the target antigen used as reference to determine peptides A.

It should be remembered that the term analogue, as used in the description and claims, means that the products involved are immunologically related.

One of the most interesting aspects as far as the biological applications are concerned resides in the fact that these peptides of group B are capable of inducing antibodies susceptible to form an immune complex, such as shown by the techniques of Western Blot, with the protein(s) of same frequency (frequencies) expressed by the infectious agent. These antibodies can correspond to antibodies induced by the peptides of type A.

Peptides of group B are also capable of inducing antibodies, or lymphocytes, recognising the autoantibodies, or the autoimmune lymphocytes, directed against the CD4.

According to an embodiment of the invention, the peptides B described above constitute, more specifically, analogues of proteins expressed by viruses with negative RNA, viruses with positive RNA, viruses with double-stranded RNA or also DNA viruses such as herpes or the cytomegalovirus, and their variants.

The invention aims especially at peptides mentioned above, analogues of proteins of retroviruses or antibodies formed against these proteins. As retrovirus, one can quote the lentiviruses with cytopathogenic power, and especially HIV, in particular HIV-1 and HIV-2 (responsible for pathologies in the human), SIV (in the monkey), VISNA (in the sheep), CAEV (in the goat), EIAV (in the horse), FIV (in the cat), BIV (in cattle), and their variants.

Other retroviruses include the oncornaviruses such as HTLV-1 and HTLV-2, isolated in the human, and animal retroviruses associated to leukaemia and cancers.

Most interestingly, the invention aims at peptides comprising or consisting of a sequence of amino acids such as determined by the IAP technique with regards to the sequence of a protein chosen among the proteins expressed by HIV-1.

Proteins of particular concern are those coded by the genes GAG, POL and ENV common to retroviruses, and more specifically of gp160, (precursor of the envelope, ENV); gp110/120(ENV); p66/68 (inverse transcriptase POL), p55 (precursor internal prot. GAG); p51/52 (POL-protease); gp41 (ENV); p40 (GAG precursor internal prot.), p31/34 (POL endonuclease), p24/25 (GAG, internal prot.); p17/18 (GAG, internal prot.).

According to the usual designation, gp means glycoprotein, p is used for the term protein and the numbers mentioned correspond to the molecular weight established by migration of these proteins in a gel and confirmed by the analysis of sequences of the corresponding genes.

According to the invention, the amino acid sequence of peptides of the invention, as determined by the IAP method with regards to one of the sequences of the proteins of the HIV mentioned above, shows in common with these proteins at least one characteristic frequency.

Peptides of great interest have a sequence of amino acids presenting a Fourier spectrum with at least one frequency equal to 0.1855, or close to this value, corresponding to that presented in common by the target proteins gp 160/120 and p55 expressed, respectively, by the genes ENV, and GAG of HIV-1, (as well as the protein POL, p66/68, such as that of the family LAVbru), or the proteins which derive from them as well as their fragments.

Other peptides present furthermore a frequency equal or practically equal to 0.2188, such as expressed by the fragment of the gp120 involved in the binding to the receptor CD4, designated later on by the expression fragment $gp120_{CD4}$. In particular, the invention aims at peptides having a sequence of amino acids such as determined by the IAP technique in relation to the sequence of that fragment, as illustrated in the examples.

Advantageous peptides are peptides of group A above, which present Fourier spectra with a frequency characteristic of fragment $gp120_{CD4}$, or if need be two frequencies, but in inverse phase in relation to that (those) of that fragment.

Other advantageous peptides are of group B which present Fourier spectra of which characteristic frequency (frequencies) is (are) in inverse phase to that (those) of peptides of group A.

Such peptides present the same phase as the characteristic frequency (frequencies) of fragment $gp120_{CD4}$.

Furthermore, they appear able to induce antibodies which cross react with the members of the same group.

In particular, they are able to induce antibodies recognising certain parts of the region of fragment $gp120_{CD4}$ in the conditions of the Elisa test and/or Western Blot such as described in the following examples.

Other modes of achievement of the invention are easily carried out by the man skill in the art as a function of the viral agent with which immunological recognition is desired. Said viral agent may be, for example, feline leukemia virus (in short FLV), precursors of the enveloppe polyproteine (10), (14), said polyproteine (11), (12), (13), (15), or fragments, or still T cell leukemia virus, HTLV-I or HTLV-II, the enveloppe polyprotein of said virus (16), (17) or their fragments, or Visna virus, in particular the enveloppe polyprotein, the precursor thereof (18), or fragments thereof.

Thus, the invention provides artificial peptides of group A, as determined according to IAP technique, in relation to a given sequence of proteins or fragments of one of the above viral agents, and the artifical peptides of group B, as determined in relation to peptides A, as well as the antibodies directed against said peptides.

In still another embodiment, the invention provides peptides capable of inducing antibodies directed against autoimmune antibodies and autoimmune lymphocytes, and also provides sequences of peptides analogous to thesea antibodies.

Peptides of that type are characterised by the fact that they comprise or consist of a sequence of amino acids as determined by the IAP technique with regards to viral sequences analogous to those of HLA-DR or also to those of interleukin 2, in inverse phase with regards to those of these sequences and by the fact that they are capable of inducing antibodies (or lymphocytes) recognising the antibodies (or the lymphocytes) directed against these sequences of HLA-DR and interleukin 2 respectively.

One should notice with interest that the peptides of the invention can present an immunogenicity directed against the proteins of an infectious agent susceptible to develop pathogenicity due to an infection caused by a first agent.

This is frequently the case in HIV infections where the patients become sensitive to infections called opportunistic. For example, HHV6 viruses which belong to the family of herpes or mycoplasmes (wall free bacteria) have been able to be detected in subjects infected by HIV.

The invention therefore aims specifically at peptides, as defined above, capable of inducing antibodies susceptible to form an immunological complex with proteins of such infectious agents, or capable of reacting themselves with these proteins. It also aims at artificial peptides, mentioned above, capable of inducing lymphocytes susceptible to react with the proteins of infectious agents.

From another viewpoint, other peptides in the invention are such as expressed by the sequences of nucleotides deduced from specific amino acid sequences as determined by the IAP technique.

These nucleotide sequences are new products which are also part of the invention.

The invention thus aims at fragments of polynucleotides characterised by the fact that they comprise or are constituted by a coding sequence for a peptide as defined above. It should be stressed that these sequences can differ, in particular because of the degeneration of the genetic code and of the coding of the same amino acid by different codons.

Other polynucleotide fragments of the invention correspond to, or are made up of sequences complementary to the above sequences, or of nucleotide sequences susceptible to hybridize with one of the nucleotide sequences complementary to those of sequences deduced from peptide sequences.

Nucleotide sequences which are particularly aimed at in the invention, correspond to those coding for the sequences of peptides of group A.

Other sequences specially aimed at in the invention correspond to those coding for the sequences of group B. One would mention in particular those coding for the sequences immunologically related to the proteins of HIV.

Other preferred sequences correspond to nucleotide sequences complementary to sequences capable of coding for the peptides of group A or of group B. These peptides coded by said complementary sequences are new products and are also part of the invention.

Said peptides are designated in the description and the claims by letter c, cA and cB, thus respectively designating peptides the sequences of which are deduced from the ARN sequence complementary to the one of the ARN sequence corresponding to peptides of group A or B respectively, and determined by using the genetic code.

It will be noticed that peptides cA form a sub-group of peptides B and peptides cB a sub-group of peptides A. Finally, peptides of type A and B coded by sequences complementary to those able to code for peptides cA and cB respectively are also in the scope of the invention. Peptides of this kind are given in the examples and designated as peptides A11 and B11.

In a very advantageous embodiment, the nucleotide fragments mentioned above are furthermore made of one or several sequences susceptible to code for one or several proteins having a biological activity presenting a particular interest for a given application.

Are also included in the invention expression vectors namely plasmid or phage, and their cellular hosts, transformed or transfected, which are generally used in the techniques of genetic engineering, and which possess the coding nucleotide sequence as defined above.

As indicated above, the peptides of the invention are capable of inducing antibodies which crossreact with the members of a same group.

These antibodies are new products and are also part of the invention.

The invention also aims at a method to obtain the peptides defined above.

According to this procedure, one can obtain by synthesis a chain of amino acids as determined by the IAP technique, as a function of the amino acid sequence of the target antigen and of a parameter, in particular one or several periodic elements characteristic of the target antigen.

As a characteristic parameter, one determines preferably the dominant frequency (frequencies) common to several proteins in the Fourier spectrum. For this, one utilises numerical analysis of amino acid sequences of the target antigen by replacing each amino acid of the sequence by an appropriate numerical value, one uses the transformation of Fourier of this set of values, and multiplies between them the Fourier spectra, obtained for the target antigen and the proteins of the same group or family or of the same biological activity as that of the antigen, thus allowing to deduce one or several common frequencies, characteristic of a group of proteins or of a given biological activity.

As numerical value, one uses preferably the value representing the equivalent of the energy of the delocalised electrons of each residue of amino acids, especially a value corresponding to the potential of interactions between the electrons and the ions.

According to one aspect of the invention, the sequence of the concerned peptide is determined on the basis of the sequence of a protein or a fragment of a protein of the viral agent, taking into account the characteristic frequency (frequencies) of that protein or of its fragment, which determine(s) the immunoreactive recognition.

In another embodiment, one uses, as reference, the sequence of a peptide determined as indicated above.

To prepare peptides of group A, that is to say analogues of antibodies directed against the target antigen, the phase of the retained characteristic frequency (frequencies) is inversed with regards to that of the frequency (frequencies) of the target antigen.

A new inversion of phase is done to prepare peptides of group B analogous to the image of the target antigen, the sequences of which are determined with regards to those peptides of group A.

Thanks to the invention, it is possible to produce peptides analogous to idiotypic antibodies directed against the target antigen, or also, of peptides analogous to anti-anti-idiotypic antibodies, vis-a-vis the target antigen. In another way, the invention supplies peptides analogues to images of target antigens, that is to say analogues of anti-idiotypic antibodies.

One should notice with interest that by using this procedure to obtain analogues of antibodies, it is possible to avoid the consecutive production of idiotypic antibodies AC1 and anti-idiotypic (antibodies) AC2, as described above, and during their administrations, the inconveniences relative to immunosuppressions or to other immunological perturbations related to the injections of antibodies.

The synthesis of peptide sequences is advantageously realised following classical techniques.

As mentioned above, these peptides are capable of inducing antibodies which crossreact with members of a same group.

The way to obtain these antibodies is also part of the invention. In a classical way, one can immunise animals using the artificial peptides defined above, then one can recover the antisera produced which possess the polyclonal antibodies. The monoclonal antibodies can be obtained if one desires by using with advantage the technique of Kohler and Milstein described in Nature 1975, vol.256 page 295.

The fragments of nucleic acids of the invention are obtained advantageously, by classical synthesis, for example by using commercially available synthesizers using the technique of phosphoramide. They can also be obtained by the technique of PCR amplification using primers of sequences of appropriate lengths. This technique of genetic amplification is described in the patents U.S. Pat. Nos. 4,683,195 and 4,683,202.

These primers built from nucleotide fragments of the invention can be used for the synthesis of artificial peptides as defined above.

As an example, such a procedure of peptide synthesis of the invention comprises the chemical synthesis of the nucleotide sequences or the amplification of nucleotide sequences capable of coding for a given peptide by contacting these sequences with at least one couple of appropriate primers, followed by the translation of sequences so amplified, in the usual way.

This last stage is advantageously achieved by transforming utilised host cells, using vectors containing the amplified sequences, and recovering the peptides produced in the host cells.

The analysis of peptides and antibodies of the invention, using classical immunological techniques such as Elisa or Western blot, has shown their high specificity in the biorecognition of molecules of the same frequency and phase.

This invention thus allows the production, on the one hand of families of peptides and antibodies capable of specifically recognising antibodies formed against proteins of viral agents and, on the other hand, of families of peptides and antibodies capable of specifically recognising the proteins of viral agents.

Among the first family are the antibodies induced against peptides of group A and peptides of group B, analogues with regards to the internal image of the proteins of a viral agent. Said first family also comprises peptides cA which constitute a sub-group of peptides B.

Peptides of group A, against which the antibodies are formed, are such as determined by the IAP technique, as defined above, with regards to the protein sequence of the viral agent implicated in the pathology to study.

The frequencies which they present in common with the concerned protein of the infectious agent are in opposite phase.

Peptides of group B present amino acid sequences such as determined with regards to those of peptides of group A above. The common frequencies are in phase with that of the protein of the viral agent.

This first family can be advantageously used as a reagent for the diagnosis of a pathology by showing the presence of antibodies or lymphocytes capable of recognizing the infectious proteins.

This method of in vitro diagnosis of the presence of such antibodies is characterised by:

the contacting of a biological sample, such as a biological fluid like serum or lymphocytes of circulating blood or also an extract of biological tissue taken from the patient to study, or the animal, with antibodies induced against the peptides of group A or with peptides of group B as indicated above, including the sub-group of peptides cA, and the demonstration of a reaction of type antigen antibody, or of a reactivity with the lymphocytes between the antibodies and the lymphocytes of the sample and the peptides or antibodies of the invention, respectively.

It will be noticed that, in the case of a lymphocyte reaction when contact with the antigen, one demonstrates either a reactivity of the lymphocytes of the sample with the peptides or the antibodies used as reagents, or the reactivity of peptides or antibodies with the lymphocytes of a patient previously immunized with the peptides of the invention. The lymphocytes thus sensibilized form reagents. Such an immunization is carried out, for example, with peptides cA.

The antibodies or artificial peptides are free or fixed on a non-immunogenic support during the stage of contact.

To show that a complex has eventually formed or the reactivity of lymphocytes, one relies upon a technique classically used in immunology such as immunofluorescence, Elisa, Western Blot, or still lymphocyte stimulation and eventually the test of presence of CTL ("cytotoxic T lymphocytes").

The detection of a selective interaction between the antibodies of the sample and the artificial peptides or the induced antibodies used, or still the reactivity of the lymphocytes is proof of the existence of the pathology.

With this method of detection one can show quickly and with great sensitivity the presence, in a biological sample, of antibodies formed against the proteins expressed by a viral agent.

It also allows the demonstration of the presence of autoimmune antibodies, formed against self-antigenic sequences and of autoimmune lymphocytes.

The second family mentioned above is made of peptides of group A including cB peptides, and antibodies or lymphocytes induced against peptides of group B, the sequences of these peptides and their frequencies being defined above.

This family can easily be used to detect the presence of proteins of a viral agent.

The method of invention of in vitro diagnosis of a viral pathology in the human or animal is characterised by:

the contacting of a biological sample such as a biological fluid like serum or lymphocytes of circulating blood, or also an extract of biological tissue taken from the patient to study, or the animal, with antibodies or lymphocytes induced against the peptides of group B, or with peptides of group A such as described above including the sub-group of peptides cB, and the demonstration of a reaction of type antigen-antibodies or of a lymphocytar reactivity between the proteins of the viral agent present in the sample and the antibodies or peptides, or the lymphocytes used as reagents.

Advantageously, said antibodies or said artificial peptides are brought into contact with the antigens of the infectious agent fixed on a support and one can induce inhibition of the reaction by competition, by adding the biological sample to be tested, when it contains the proteins of the viral agent.

To show that the complex has eventually formed or the reactivity of the lymphocytes, one relies upon one of the techniques currently used for the detection of antibodies, or the revelation of the presence of antigen(s) stimulating the lymphocytes of the animal immunized against the peptides of group B.

The detection of a selective interaction between the proteins of the sample and the induced antibodies (or the test lymphocytes) or the artificial peptides used would be an indication of the existence of the pathology.

The proteins expressed by a viral agent can thus be easily detected, localised and quantitated, for example at the level of biopsies of pathological tissue, or of cells of peripheral blood.

The invention aims also at kits for the in vitro diagnosis of viral pathologies in the human or animal.

For example, a diagnostic kit according to the invention would comprise:

antibodies induced against artificial peptides of group A or of artificial peptides of group B or of artificial peptides of group A and antibodies induced against artificial peptides of group B, as defined above, advantageously immobilised on the support, or optionally mixed, in order to detect several infections, appropriate reagents for the immunological reaction between said induced antibodies or artificial peptides and the antibodies formed against these proteins and the antigenic proteins respectively, showing furthermore that the reaction occurs, and otherwise, a biological medium of reference as a control.

In order to detect a lymphocyte reactivity, the kit according to the invention will advantageously include lymphocytes, for example under a deep frozen form, from the animal immunized against given peptides.

The antibodies and peptides used are immobilised, in a classical way, on beads, for example latex beads, microtiter plates, or also strips.

Furthermore, the invention deals with the application of peptides as defined above for the production of immunogenic compositions.

Immunogenic compositions preferred comprise at least one peptide of group A of which the characteristic frequency (frequencies) in the Fourier spectrum are in opposite phase to that (those) of the antigenic sequence responsible for the autoimmune pathology. The amino acid sequence of these peptides of group A is such as determined by the IAP technique with regards to the antigen to be treated.

It deals with peptides capable of inducing antibodies susceptible to neutralize autoimmune antibodies and to destroy autoimmune lymphocytes.

Other preferred immunogenic compositions are characterised by the fact that they comprise at least one peptide of group B, in association with an acceptable pharmaceutical vehicle for the production of vaccines. Following classical techniques, the immunogenic peptide can also be expressed by corresponding nucleotide sequences incorporated in an infectious agent, the safety of which has been first established, such as a recombinant virus like those prepared from viruses of the family of poxviruses. A virus of this type largely used is constructed by the vaccine produced from a living strain, attenuated or killed.

The immunogenic composition is administered according to a protocol and in such quantity as to induce in the host immunity against the antigens of the infectious agent.

Such a composition can be used to produce vaccine capable of inducing sensitised lymphocytes and antibodies directed against the infectious agent.

Compositions which are particularly aimed at have a peptide of group B, such as determined by the IAP technique, with regards to a peptide of group A itself determined with regards to proteins of a virus, in particular with regards to those of a retrovirus, namely HIV.

As mentioned above, this group comprises peptides cA.

One aspect of high interest is that only one peptide is capable of inducing antibodies which recognise all the proteins of the viral agent which express in common a significant periodic element.

Such immunogenic composition vis-a-vis HIV is quantitated in terms of antigenic peptide in such a way as to allow the administration of a dose between 10 and 100 $\mu$g/kg.

Lymphocytes sensitised by artificial peptides of group B, analogues of the image of the target protein, correspond to the category of immune lymphocytes carrying receptors involved in the destruction of the infectious agent or the cell infected by it, as these receptors are capable of recognising the antigen. In this case, the activity of the CTL ("Cytotoxic T Lymphocytes") or other types of lymphocytes which do not require mediation of antibodies, sensitised with the anti-idiotype, is not subjected to a restrictive control of the genetic identity of MHC, and in consequence should not represent any obstacle to the destruction of infected target cells, or of the infectious agent (2).

On the other hand, antibodies induced by the peptide analogous to the internal image can intervene in the function of complement as well as in the activity called ADCC ("Antibody-Dependent Cell-mediated Cytotoxicity") of cytotoxic lymphocytes (lymphocytes K) destroying the cells which carry on their surfaces antibodies taken up by the antigens. Contrary to the immune response to cellular mediation lymphocytes K have no specificity against the antigen, but they possess a receptor for the fragment Fc of IgGs and their lytic activity does not require the complement.

The peptides in the invention and the antibodies against these peptides can also be used in therapy, in particular as drug or antigen vectors. In the case of antigens coupled to peptides of the invention, any bacterial or viral antigen may be used, inasmuch as the organism was previously immunized (or vaccinated) against this one.

The vectors must be designed in relation to the molecular domains of the target proteins (viral antigens) which do not interact with cellular elements in the process of virus/cell recognition.

This feature is essential in order to avoid the induction by the vector of antibodies which could recognise the cellular structures with which the target protein interacts.

The invention relates to the use of type A peptides as drug vectors and type B peptides as inducers of antibodies or cytotoxic lymphocytes capable of intercepting the antibodies/lymphocytes directed against CD4.

Other characteristics and advantages of the invention will be shown in the following figures.

BRIEF DESCRIPTION OF THE FIGURES

FIG. 1*a* represents the Fourier spectra of HIV protein.

FIG. 1*b* represents the Fourier spectra of HIV protein.

FIG. 1*c* represents the Fourier spectra of HIV protein.

FIG. 1d represents the Fourier spectra of HIV protein.

EXAMPLE 1

ANALYSIS OF PROTEINS OF A VIRAL AGENT BY THE IAP TECHNIQUE

Establishment of a Numeric Sequence

Figure 1A:
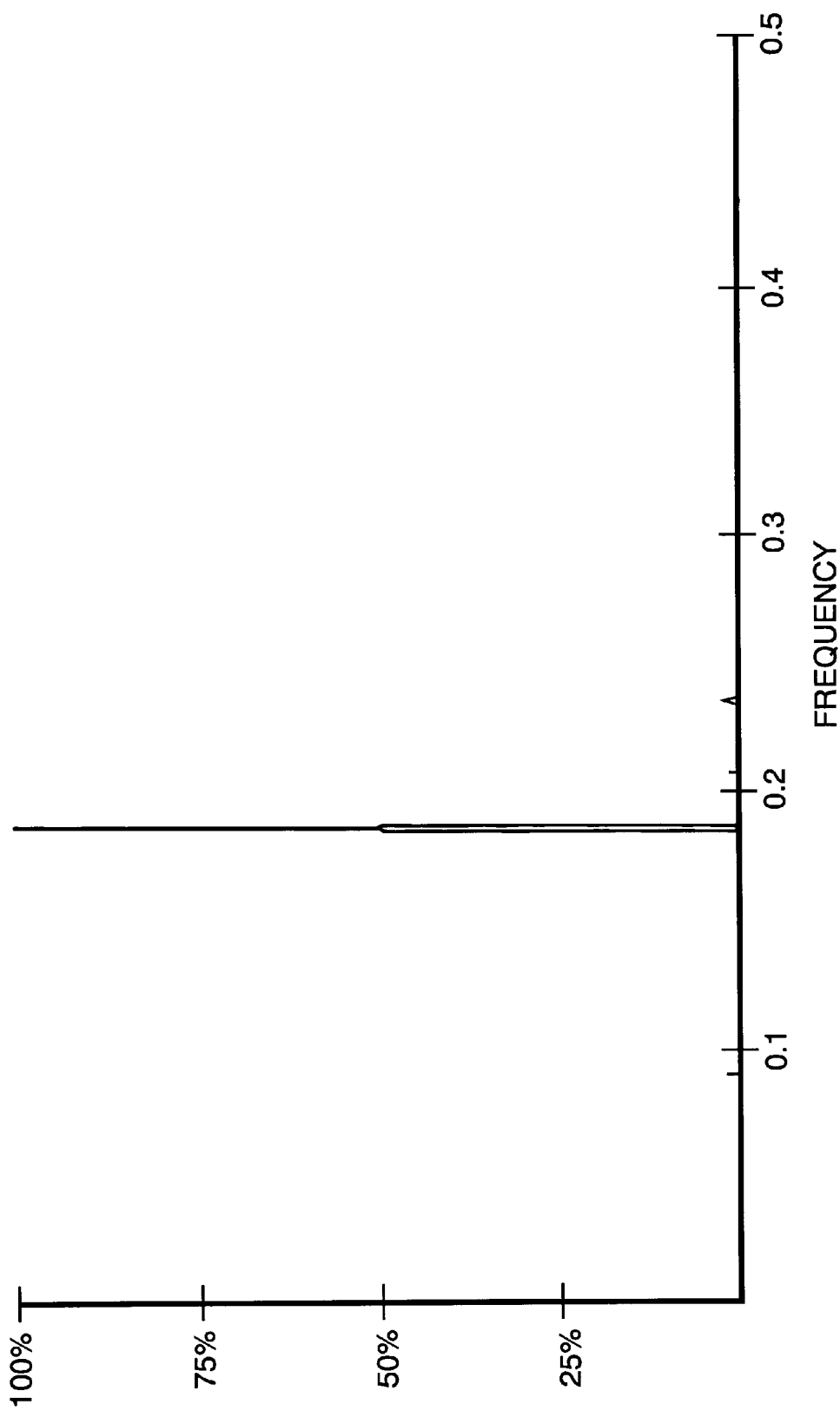
FIG. 1e represents the Fourier spectra of HIV protein.
FIG. 1f represents the Fourier spectra of HIV protein.
Figure 1B:
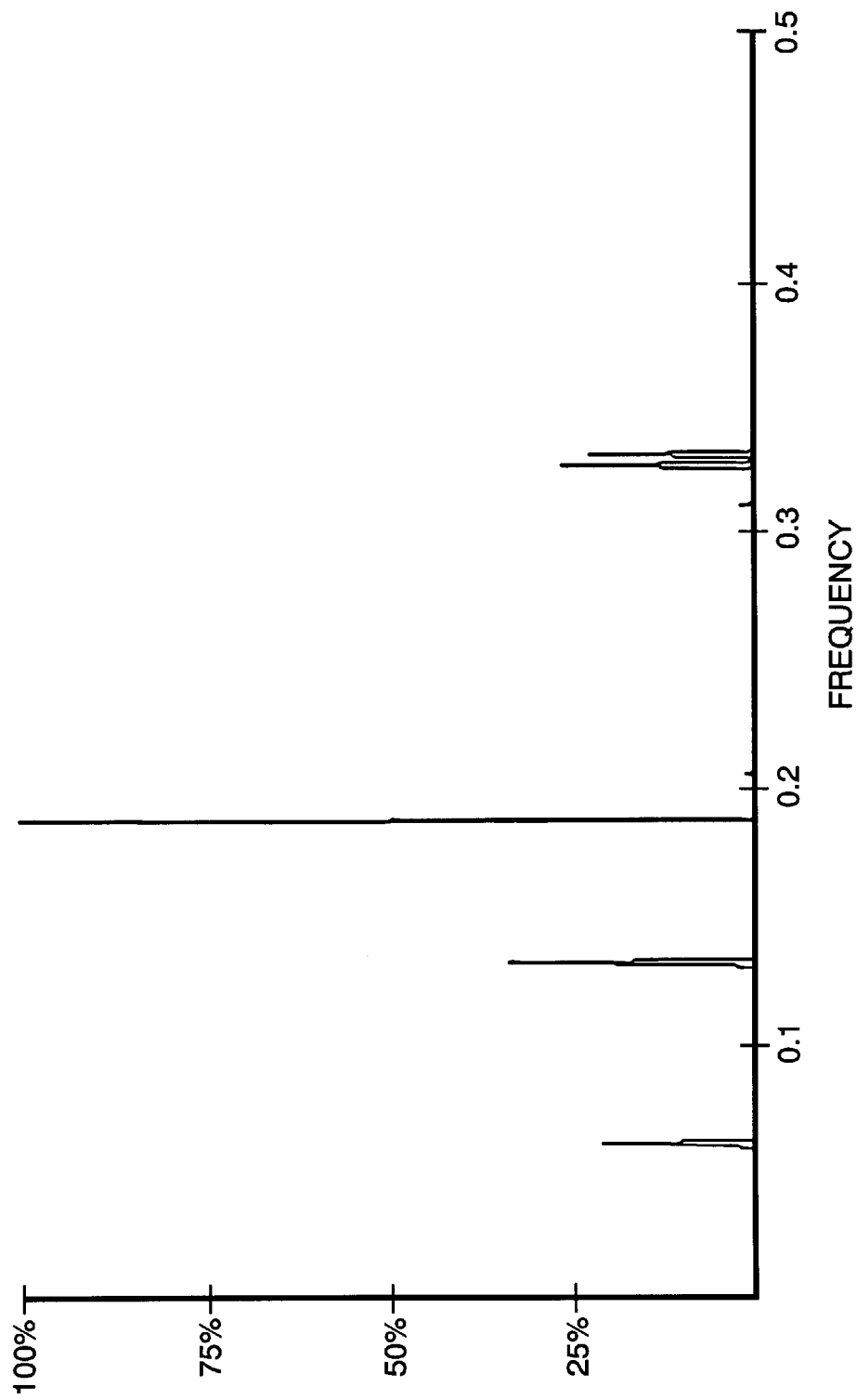
Figure 1C:
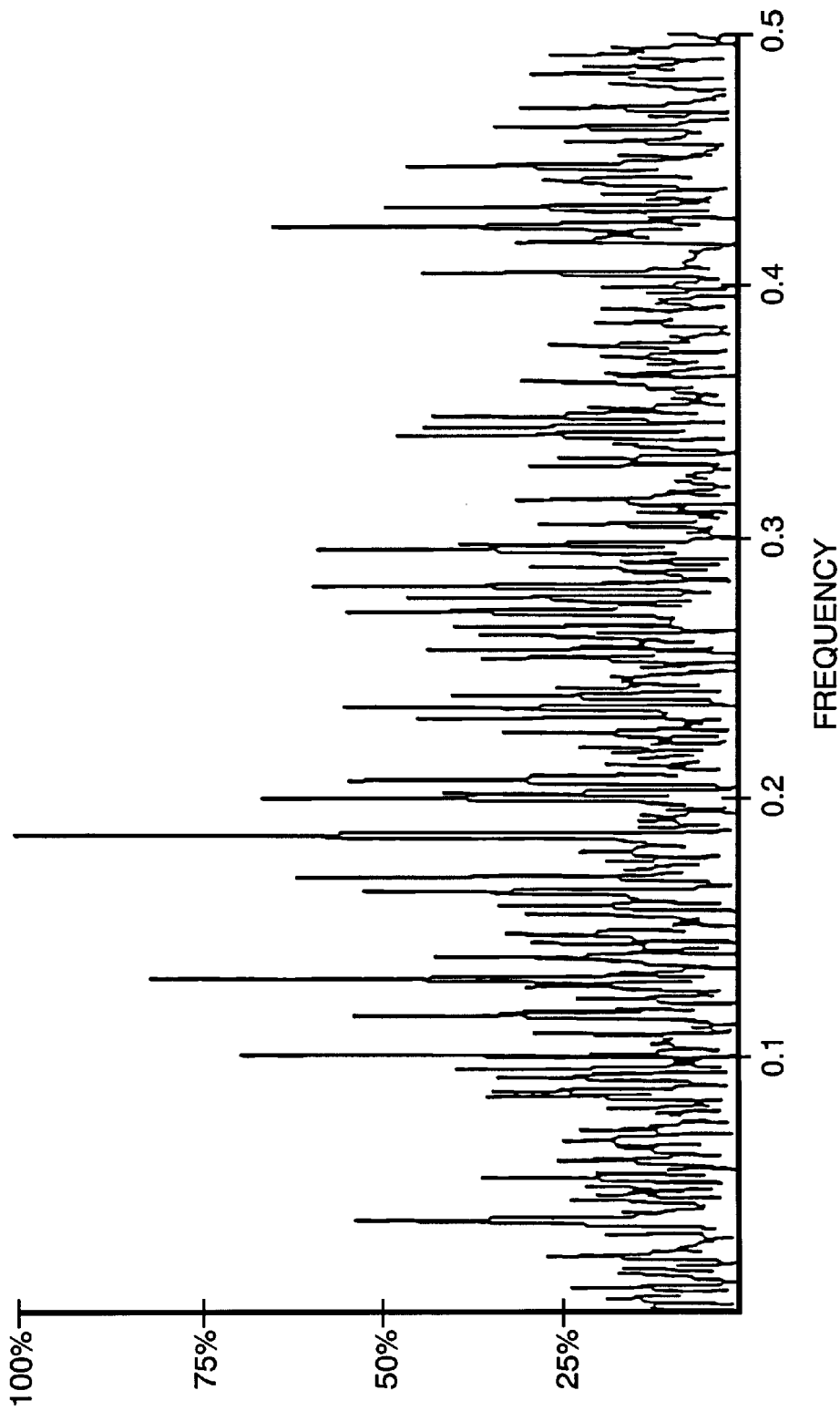
Figure 1D:
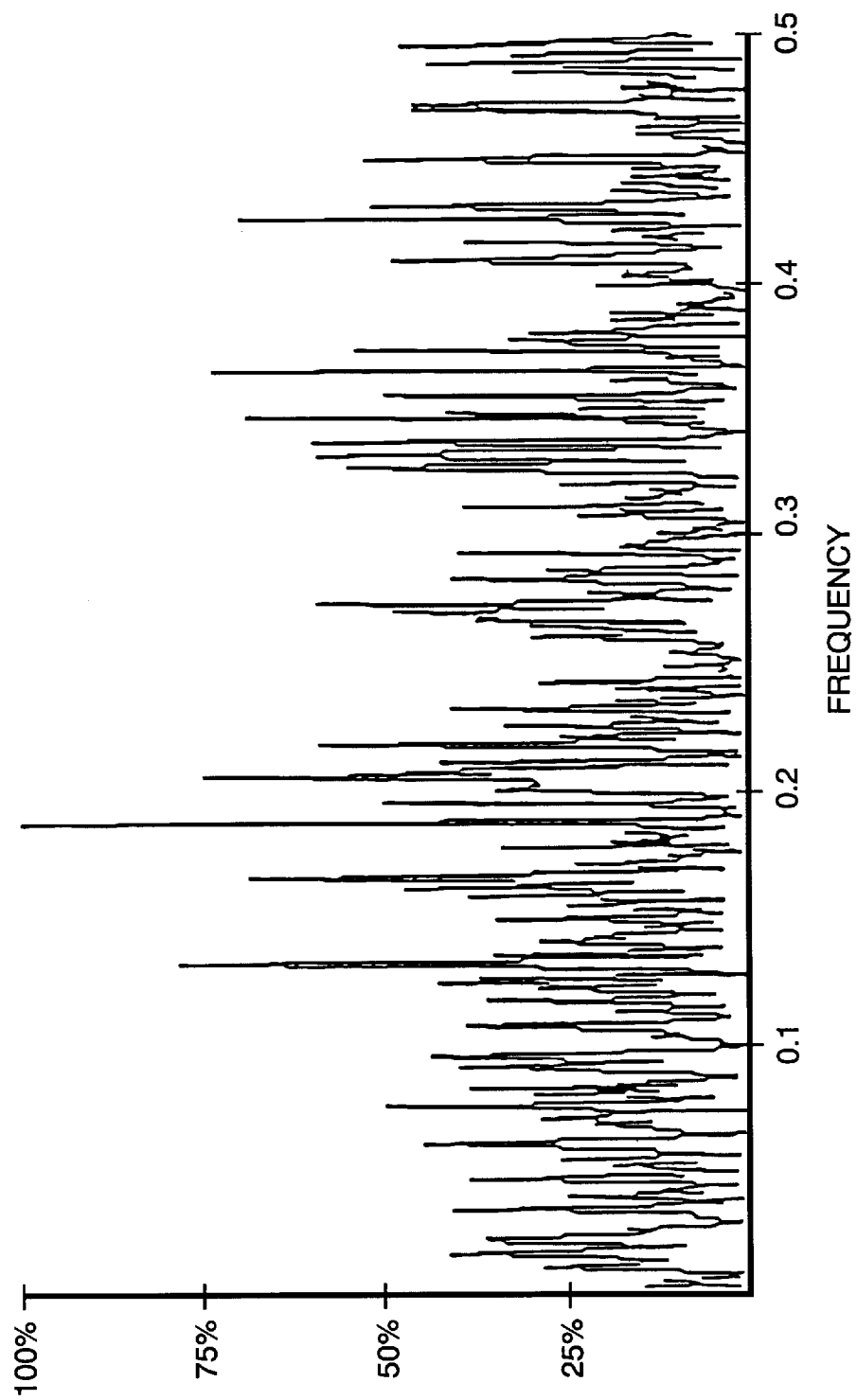
Figure 1E:
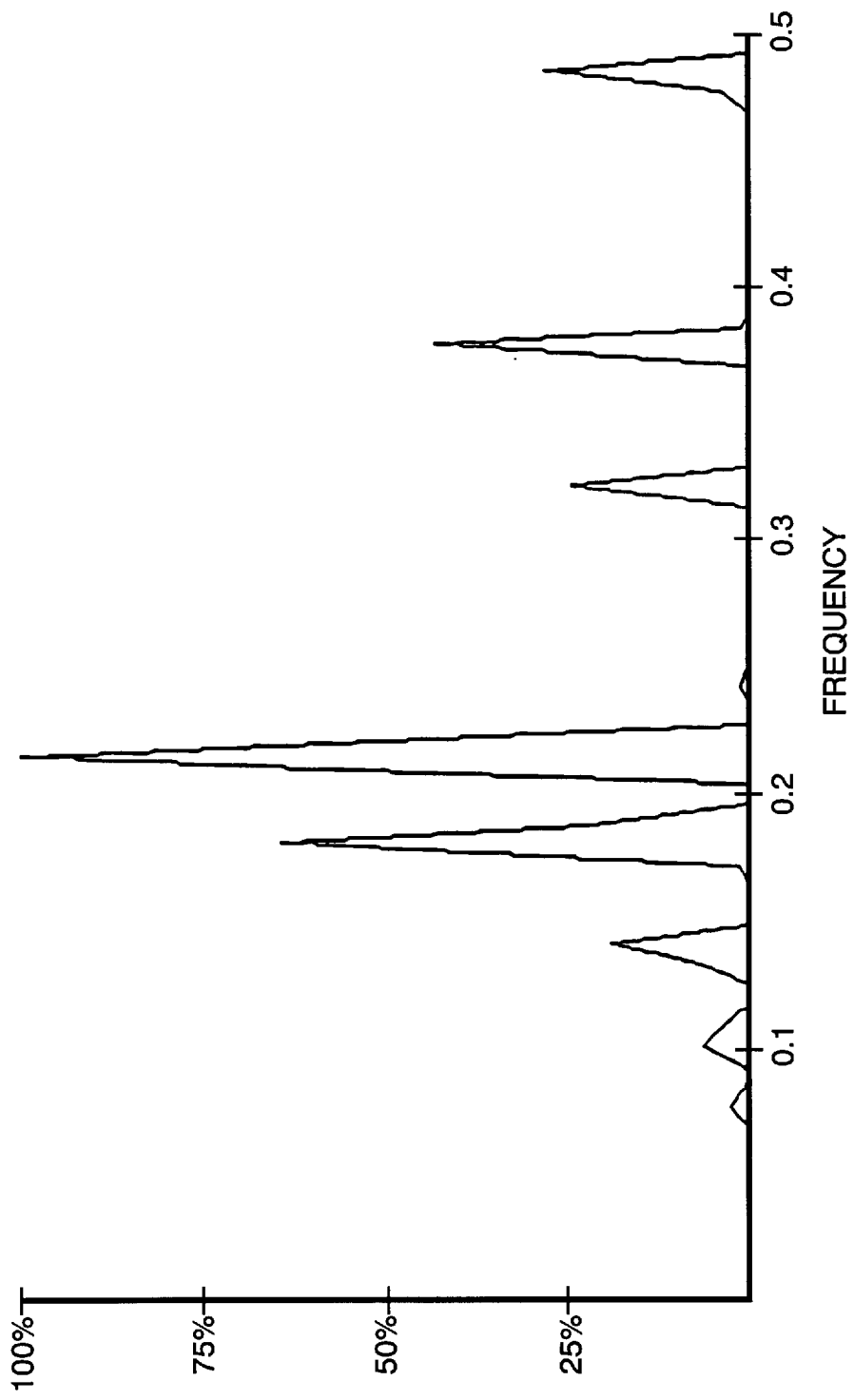
Figure 1F:
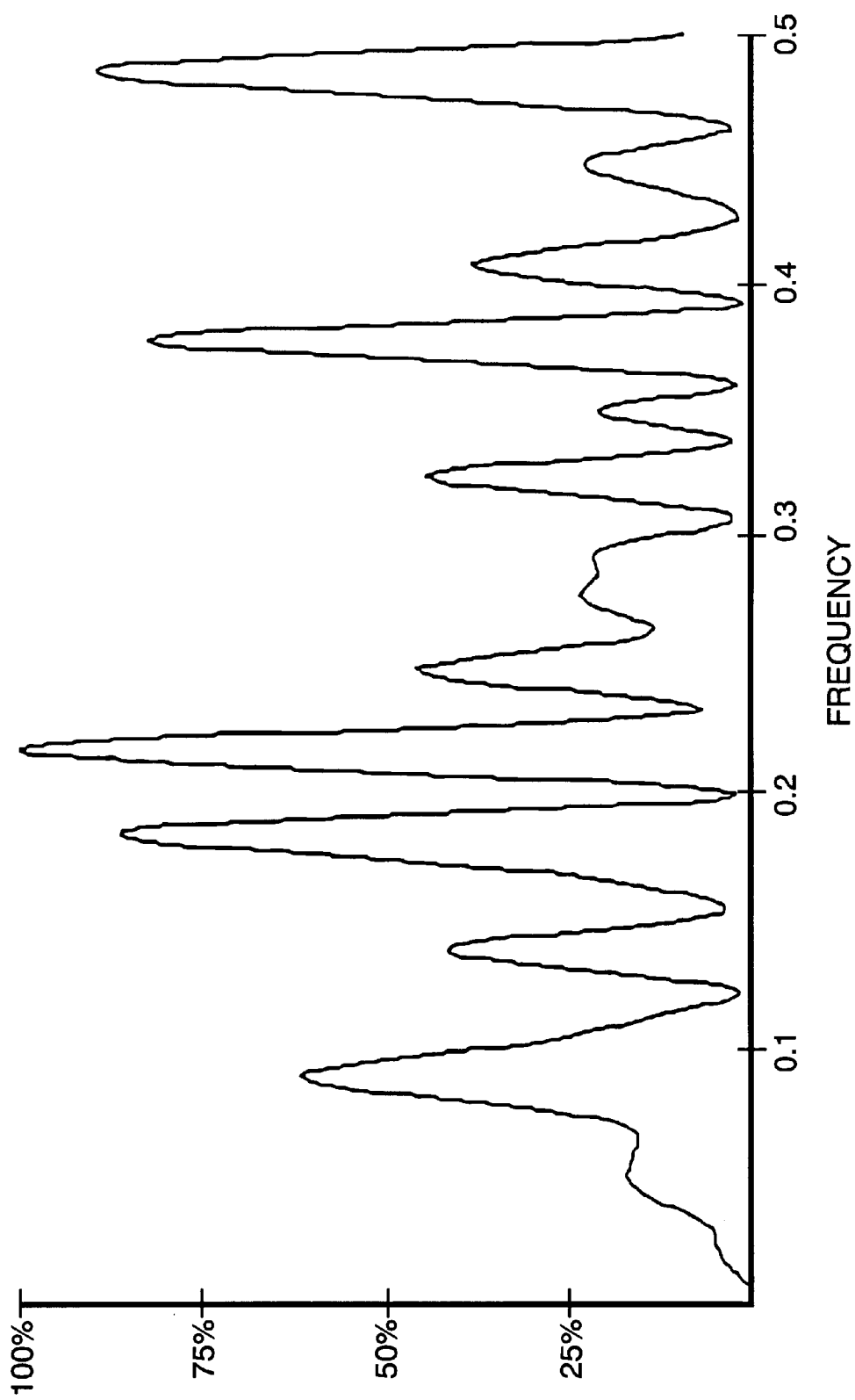

According to the IAP technique, one can calculate the apparent potential, or pseudopotential, of each of the amino acids of a given protein sequence according to the following general formula (4):

$$W = 0.25 Z^* \sin(1,04 \pi Z^*)/2\pi, \quad (1)$$

where $Z^*$ represents the average of the number of quasivalences determined by $$Z^* = \sum_{i=1}^{N} Z_i / N \quad (2)$$

where Z represents the number of valence electron of the ith atom of the molecule and N the total number of atoms in the molecule.

The values of PEII (5) so calculated for the 20 natural amino acids are represented in table 1. The value attributed to an amino acid remains unchanged no matter what its position in the sequence of the protein.

TABLE I

| Amino Acids | PEII (Ry*) |
|---|---|
| Leu (L) | 0.0000 |
| Ile (I) | 0.0000 |
| Asn (N) | 0.0036 |
| Gly (G) | 0.0050 |
| Val (V) | 0.0057 |
| Glu (E) | 0.0058 |
| Pro (P) | 0.0198 |
| His (H) | 0.0242 |
| Lys (K) | 0.0371 |
| Ala (A) | 0.0373 |
| Tyr (Y) | 0.0516 |
| Trp (W) | 0.0548 |
| Gln (Q) | 0.0761 |
| Met (M) | 0.0823 |
| Ser (S) | 0.0829 |

TABLE I-continued

| Amino Acids | PEII (Ry*) |
|---|---|
| Cys (C) | 0.0829 |
| Thr (T) | 0.0941 |
| Phe (F) | 0.0946 |
| Arg (R) | 0.0959 |
| Asp (D) | 0.1263 |

*Ry* = Rydberg unit

Fourier Transformation

The Fourier transformation is performed as follows:

$$X(n) = \sum_{m=1}^{N} x(m) e^{-j(2\pi/N)n,m} \quad n = 1, 2 \ldots N/2 \quad (3)$$

Where x(m) is the mth member of the analysed numeric sequence, N is the total number of points in the sequence and X(n) is the nth coefficient of the Fourier transformation (6).

The numeric series utilised for the Fourier transformation thus represents discrete "determinant" signals of finite lengths. The absolute values of the coefficients of the Fourier transformation define the amplitude of the spectrum, whereas their phases define the phase spectrum as follows:

$$X_{(n)} = |X_{(n)}| e^{-j\Phi(n)} \quad n=1,2 \ldots N/2 \quad (4)$$

Therefore, the complete information of the original sequence is contained in the two spectral functions.

However, in the case of a protein sequence, the information can be contained only in one of those two spectral functions. In this case, it is more practical to analyse the energy density of the spectrum called informational spectrum, which is defined as follows:

$$S_{(n)} = X_{(n)} X^*_{(n)} = |X_{(n)}|^2 \quad n=1,2 \ldots N/2 \quad (5)$$

The analysed sequences in terms of discrete signals are determined at equidistant points of a distance d=1, in such a way that the maximum frequency is F=1/2d=0.5. The extent of the frequency is independent of the number of points in the sequence; the latter plays a role only on the resolution of the spectrum. At a point N of the sequence, the resolution r is equal to 1/N (6) and the n-th point of the spectral function corresponds to a frequency fn=n/N. The minimum number of points required for an analysis is determined according to the desired resolution of the spectrum (that is to say according to the number of peaks to demonstrate).

Multiplication of Spectra

The demonstration of common characteristic periods for two or several proteins having a similar function can be done by mutually multiplying the respective Fourier spectra (convolution product) in order to get a so-called cross-spectral function. This crossed spectral function, from which a frequency common to both signals can be seen, is defined as follows:

$$S_{(n)} = X_{(n)} Y^*_{(n)} \quad n=1,2 \ldots N/2 \quad (6)$$

Where $X_{(n)}$ represents the coefficients of the Fourier transformation of the series x(m) while Y(n)* represents the complex coefficients conjugated of the Fourier transformation of the series y(m). The delineation of peaks, in the crossed spectrum, for certain frequency (frequencies) defines the frequency common to both compounds. On the other hand, a multiple cross-spectral function is obtained from a group of sequences as follows:

$$M_{(n)} = X_1(n) \cdot X_2(n) \ldots XM(m) \quad n=1,2 \ldots N/2 \quad (7)$$

EXAMPLE 2

Application of the technique in example 1 to the analysis of HIV proteins:

The algorithmic procedures were applied to the HIV gp160 (ENV) protein sequences, HIV p55 (GAG), a 44 mer fragments of HIV gp 120 involved in CD4 recognition (7), and the murine and human CD4 protein.

In line with example 1 method, the analysis procedure comprises the following steps:

1. each amino acid sequences was converted to the related numerical series by representing each amino acid with the corresponding value of the electrom-ion interaction potential,
2. this numerical series was converted into a numerical spectrum using FFT;
3. spectra were mutually compared using cross-spectral analysis with the aim to extract common frequency components.
4. multiple cross-spectral analysis was then applied over each group of the protein sequences gp160 (ENV), p55(GAG), 44 amino acid fragment of gp120 to extract common characteristic frequency components for the CD4 biorecognition by protein gp120.

Once the characteristic Fourier spectral frequency for the HIV-1 protein family had been found, it was possible to predict via an inverse procedure the specific amino acids in the particular sequence which predominantly contributed to this frequency and which were likely to be crucial for the observed protein pattern.

With the characteristic Fourier frequency of the HIV-1 and gp120 fragment recognising CD4 it was also possible using analogous methods to identify a variety of analogous peptides which have the same desired spectral characteristics. These polypeptides were designed de novo or as fragments related to the HIV-1 BRU variant proteins. With the de novo designed polypeptides, rigorous criteria were employed to ensure that each de novo polypeptide had the characteristic Fourier frequency(ies) and phase(s).

The procedures and criteria for the design of these peptides, involved the following steps:

5. Determination of the characteristic frequencies for the analyzed group of HIV-1 proteins as described above in Steps 1–4;
6. definition of the characteristic phases at the characteristic frequencies for the gp120 HIV-1 BRU isolate, chosen as protein for peptide design;
7. derivation of a new numerical sequence from the knowledge of these characteristic frequencies and phases using inverse discrete Fourier transform procedures,
8. determination of the amino acid corresponding to each element of this new numerical sequence from values of EIIP (see table 1).

Peptides obtained in this way have the same spectral characteristics as those associated with gp160/120. CD4 biorecognition and can be proposed to exhibit a similar set of functional pattern-properties. For example, polyclonal (or monoclonal) antibodies generated against these synthetic peptide analogues should be capable of cross-reaction with the surface region of the gp160/120 protein molecule responsible for the CD4 binding.

Results obtained with the amino acid sequences of glycoproteins of envelop gp160/120, and those coded by the gene GAGp55 are given hereinafter.

From the analysis of cross spectra of glycoproteins gp160 obtained from various isolates of HIV-1 one can deduce a characteristic frequency which predominates in the Fourier spectra.

Therefore, as seen in FIG. 1*a*, by crossing the spectra of gp160 obtained from 21 isolates of HIV, one can detect a common frequency at f1=0.1855.

The same frequency is the major spectral characteristic for proteins p55 of the gene GAG from 11 isolates of HIV (FIG. 1*b*).

One can also find this f1 frequency as average signal in the spectrum of proteins gp160 and p55 from isolates such as LAVbru as seen in FIGS. 1*c* and 1*d*.

This characteristic frequency f1 can also be seen in the fragment of the gp120 corresponding to the amino acids 418 to 461 (numbering according to the Neosystem Laboratory 1990, HIV-peptides, SIV-peptides), responsible for the fixation to CD4 (7) of various isolates of HIV and of the isolate LAVbru. Furthermore, a frequency f2=0.2188 can also be seen in FIG. 1*e* (8 isolates of HIV) and 1*f* (isolate LAVbru) respectively.

The analysis of cross spectra of the complete sequence of gp120, as well as gp160, shows the characteristic frequency f1 but the frequency f2 does not seem to show a strong characteristic amplitude.

EXAMPLE 3

Preparation of artificial peptides of type A and type B by reference to a fragment of gp160/120.

The following examples deal with the preparation of peptide sequences of 20 amino acids, using a fragment of 44 amino acids of gp160/120, prepared from an isolate of HIV-1, i.e. the clone n143 LAVbru, which present the characteristic frequencies f1 and f2 in the IAP spectra (FIG. 1*f*).

This fragment corresponds to the following sequence, S, of amino acids (7):

S=TITLPCRIKQFINMWQEVGKAMYAPPISGQIRC SSNITGLLLTR(SEQ ID NO:1)

Preparation of peptides of group A

Peptide A1

On the basis of the S sequence of the fragment above, but inversing the phases of frequencies f1 and f2, one has determined the sequence of peptide A1 using the IAP technique of example 1. The sequence obtained is as follows:

Sequence A1=KQQYYWYAWCQPPQDQLIMD(SEQ ID NO:2)

The Fourier spectrum of this peptide A1 is represented in FIG. 2*a*.

Peptide A2

In a similar fashion, the sequence of peptide A2 has been determined by inversing the phase of the frequency f1, but without taking account in this case the frequency f2, as this peptide has been established, as far as the frequencies are concerned, only in relation to f1.

The Fourier spectrum of peptide A2 is represented in FIG. 2*b*.

The sequence of amino acids is as follows:

Sequence A2=LKRDQEPMDFHIWDDYLKRD(SEQ ID NO:3)

One can see that A1 and A2 do not show any homology, as far as their sequence is concerned, although they have in common the frequency f1.

Elaboration of Peptides of Group B

Peptide B1

This peptide has been prepared in such a way as to present the same frequencies f1 and f2 as peptide A1, but in opposite phases to these frequencies, and therefore in the same phases as the frequencies f1 and f2 of the fragment of sequence S.

The IAP spectrum of peptide B1 is shown in FIG. 2*c*.

Its sequence is as follows:

Sequence B1=DDALYDDKNWDRAPQRCYYQ(SEQ ID NO:4)

One can see that it has no homology with peptides A1 or A2.

Peptide B2

Figure 2A:
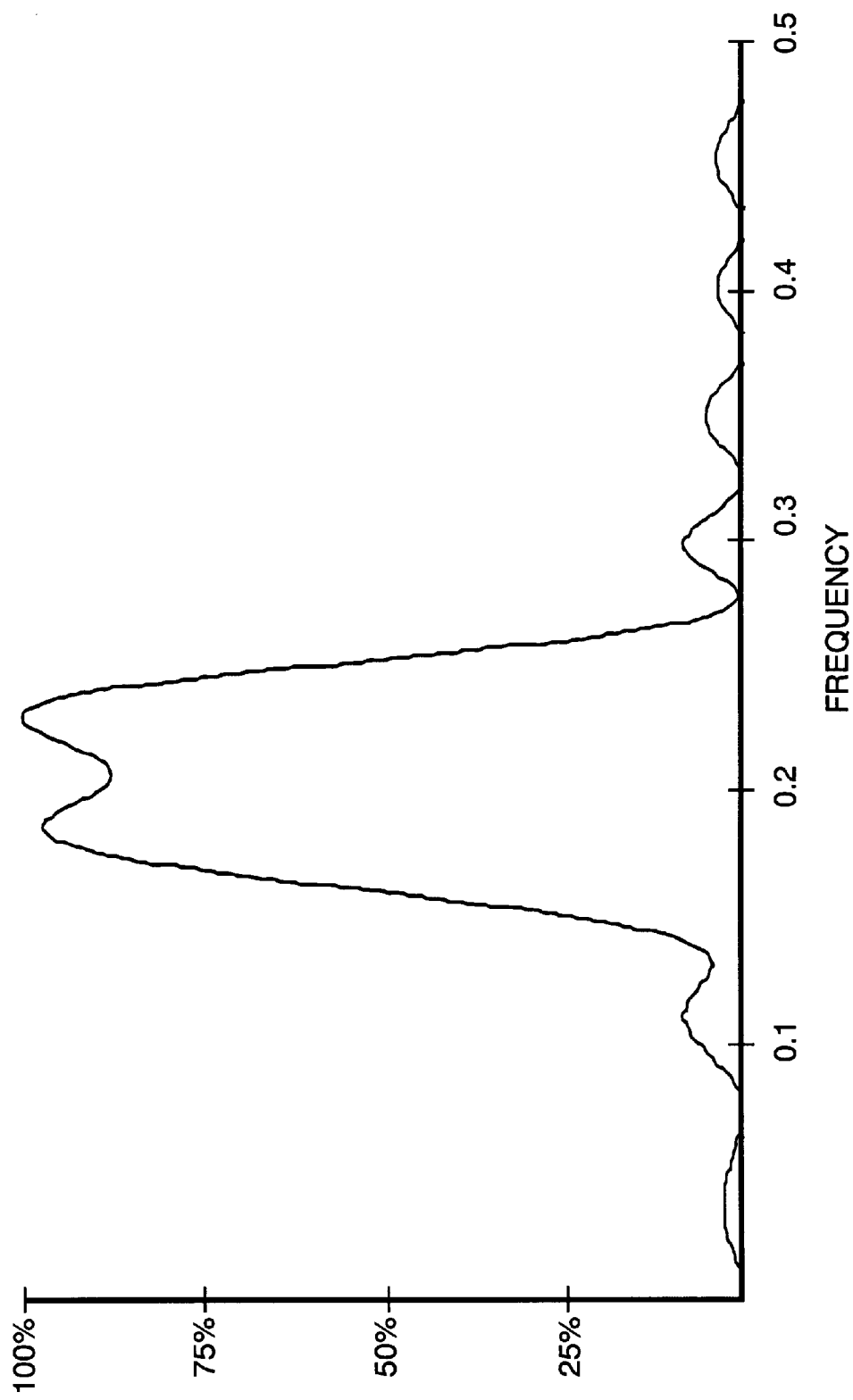
FIG. 2a represents the Fourier spectra of artificial peptide of the invention.
Figure 2B:
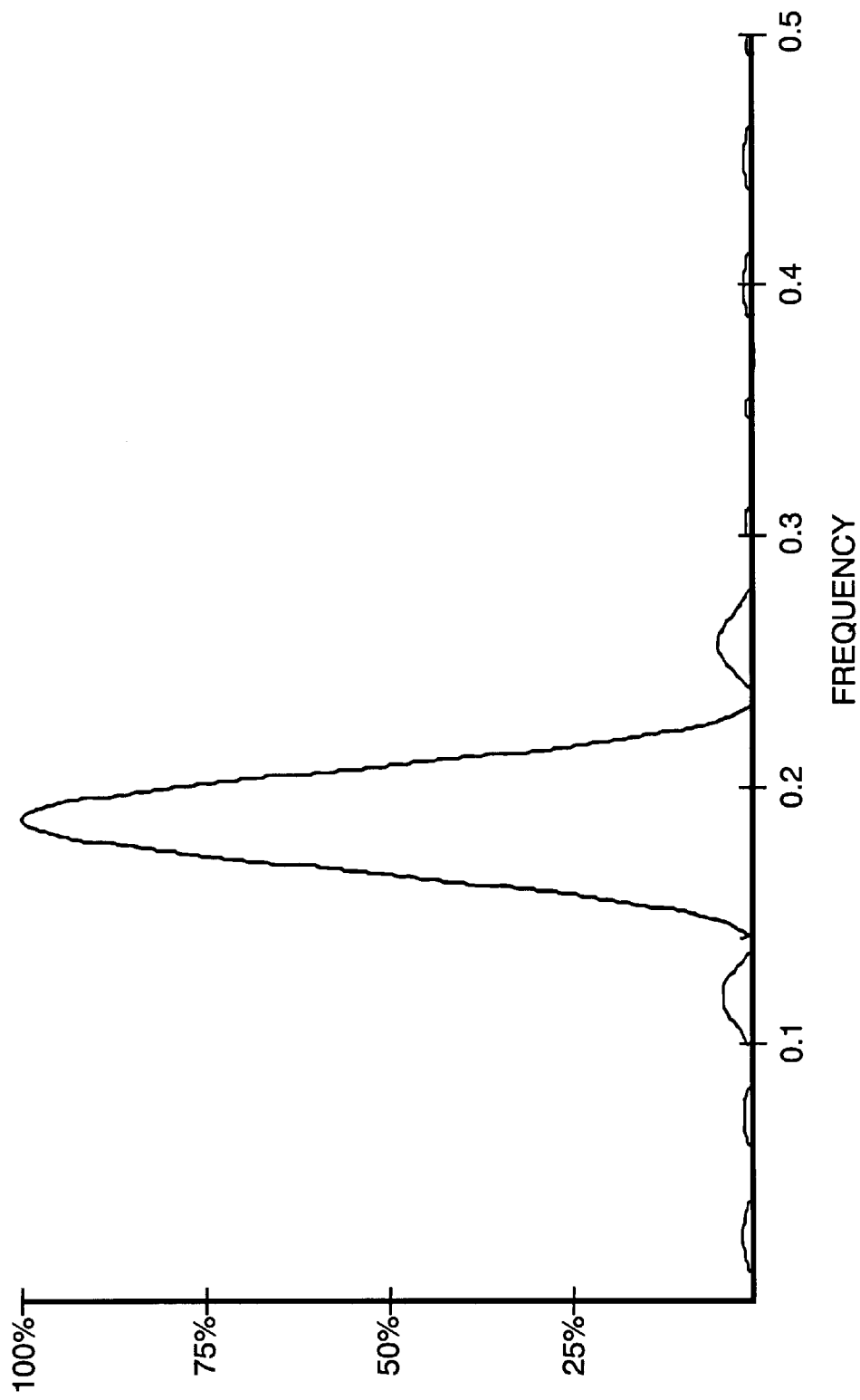
FIG. 2b represents the Fourier spectra of artificial peptide of the invention.
Figure 2C:
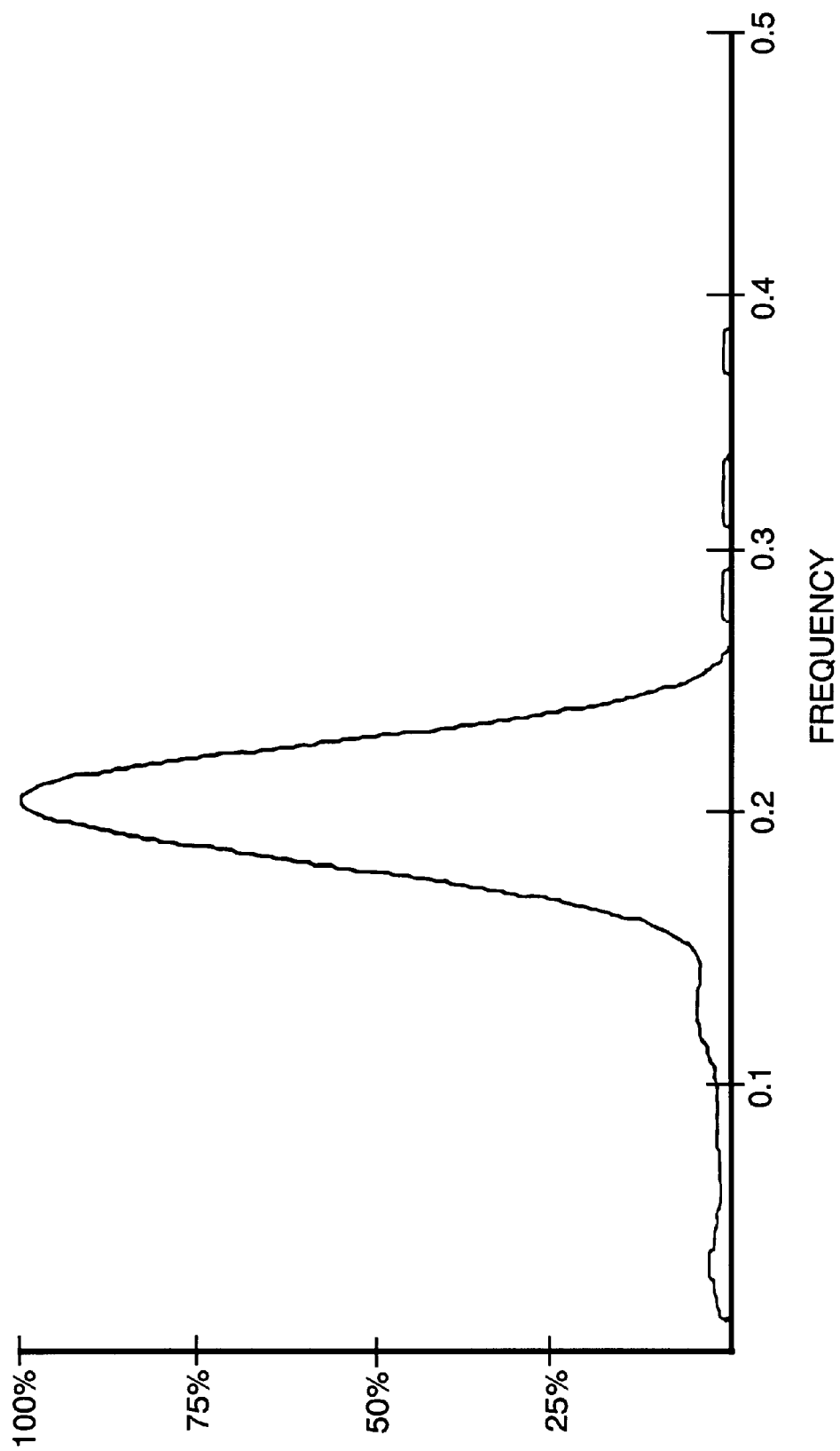
FIG. 2c represents the Fourier spectra of artificial peptide of the invention.
Figure 2D:
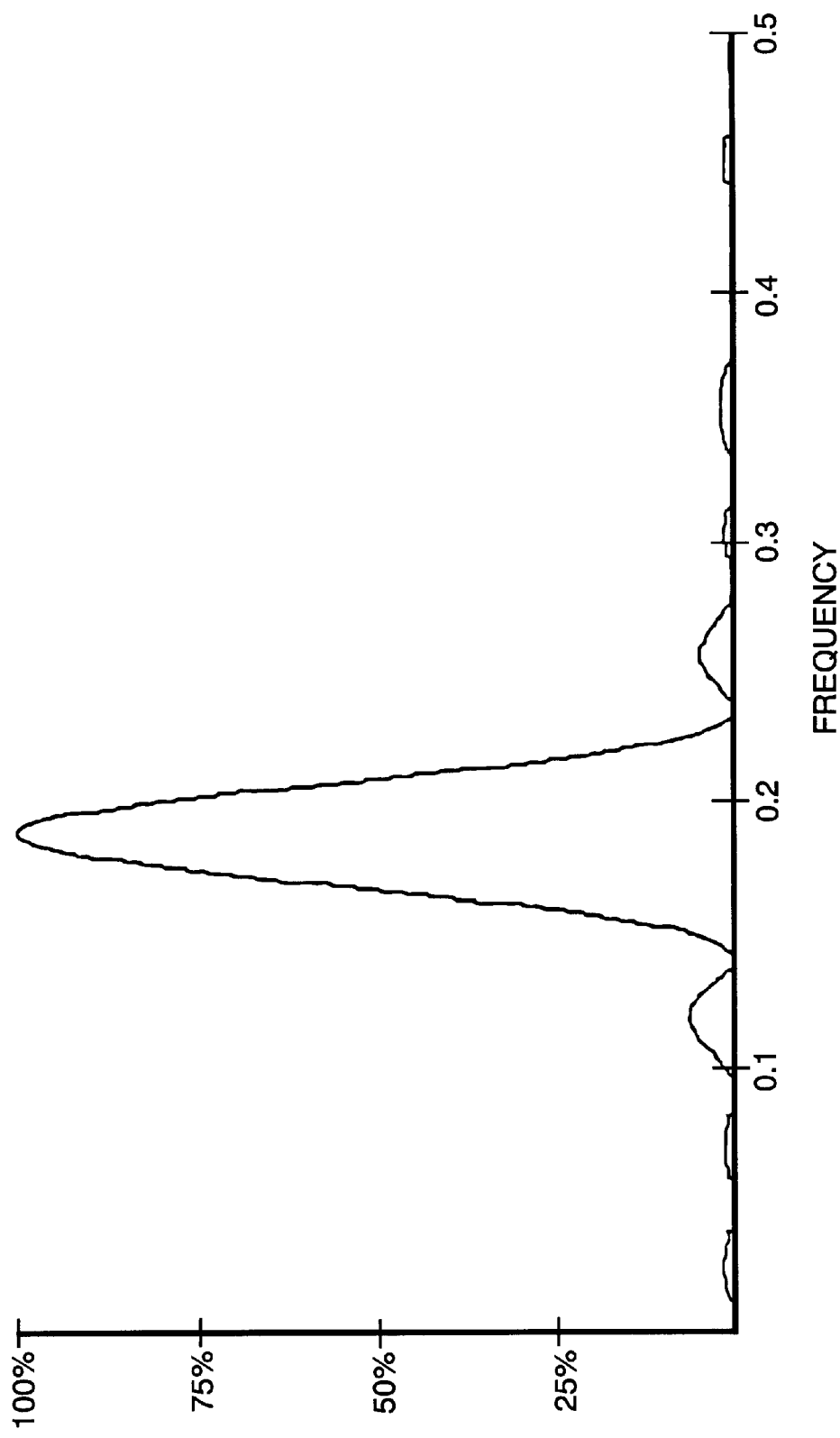
FIG. 2d represents the Fourier spectra of artificial peptide of the invention.

This peptide has been prepared by anology with peptides A1 and A2, and presents a unique frequency f1, in opposite phase to that of A1 and A2. The IAP spectrum of peptide B2 is presented in FIG. 2d.

This peptide, which has the following sequence

Sequence B2—DFHIWDDYLKRDQEPMDFHI(SEQ ID NO:5) presents the same phase as peptide B1 with the characteristic frequency f1.

EXAMPLE 4

Synthesis of Artificial Peptides from Example 3

The resins of protected peptides have been synthesised using the technique of multiple peptide synthesis developed by HOUGHTEN (8), using a resin of p-methyl-benzhydrylamine (100 to 200 mesh, 0.4 to 0.8 meg/g), and the amino acid N-α-t-butoxy carbonyl (t-boc) which are commercially available from Bachem Inc (Torrence, Calif.).

The peptides have been separated from their resin using the well known technique of hydrogen fluoride and anisole (9). After synthesis, the purity of the peptide has been evaluated by reversed phase HPLC on a column of PepRPC HR5 (Pharmacia).

The chromatograms have been developed in a gradient of 0.1% $CF_3$ $COOH/H_2O$ and $CF_3COOH/CH_3CN$ (v/v). The peptides represent approximately 85% of the material absorbing at $OD_{214}$. The peptidic sequences have been checked.

EXAMPLE 5

Application of the method of example 1 to the analysis of the retroviral feline leukemia or FLV:

The results obtained from analysis with the sequences of amino acids which constitute the glycoproteins of the FLV envelop polyprotein obtained from different isolates, i.e. the so called knob glycoproteins, knob gp 70, the so called spike proteins (spike p15), and the FLV T-Cell receptor protein permitted determination of the predominant characteristic frequencies from the Fourier spectra. The results are given on FIGS. 3a to 3f.

Figure 3A:
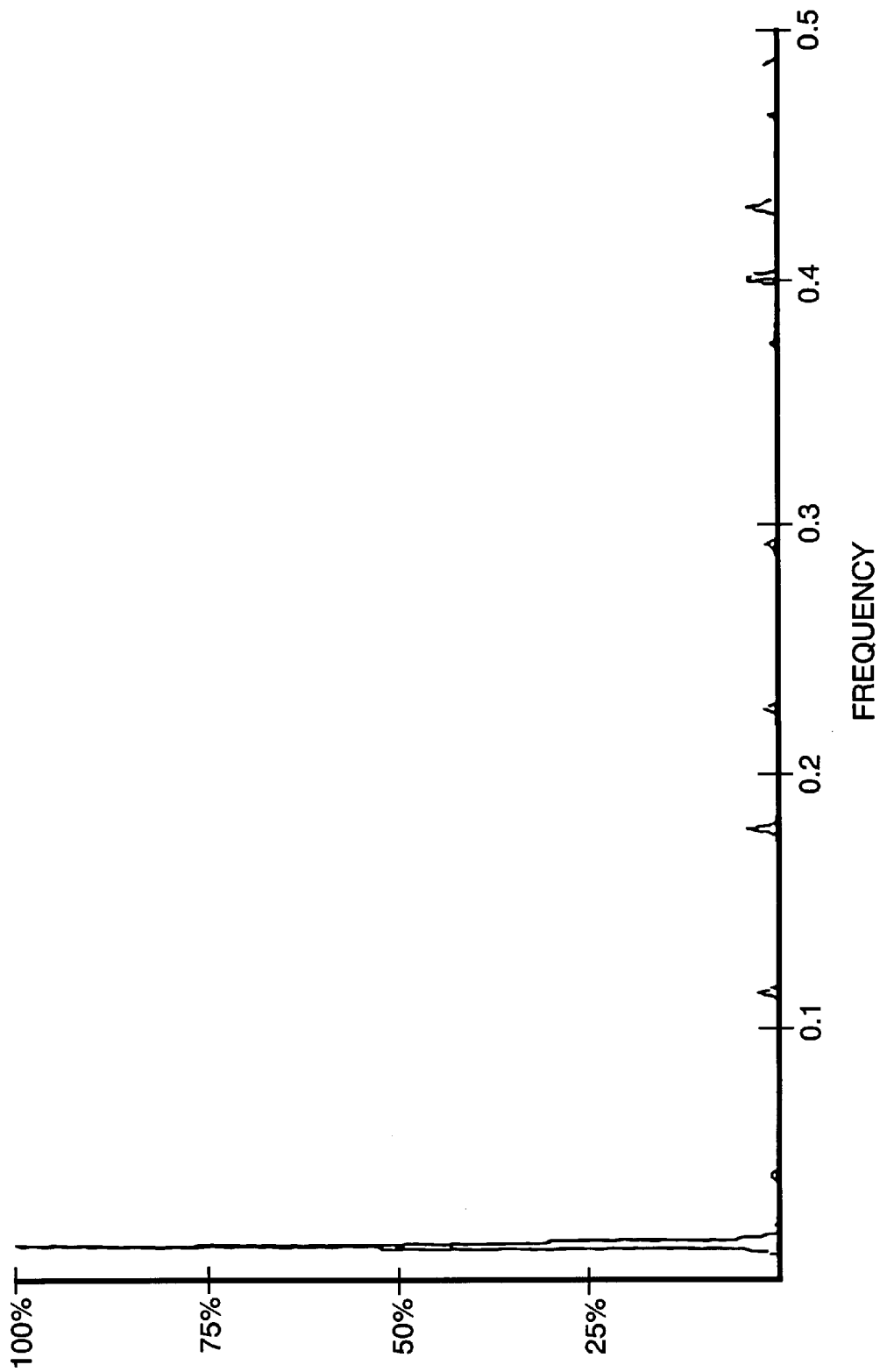
FIG. 3a represents the Fourier spectra of FLV protein.
Figure 3B:
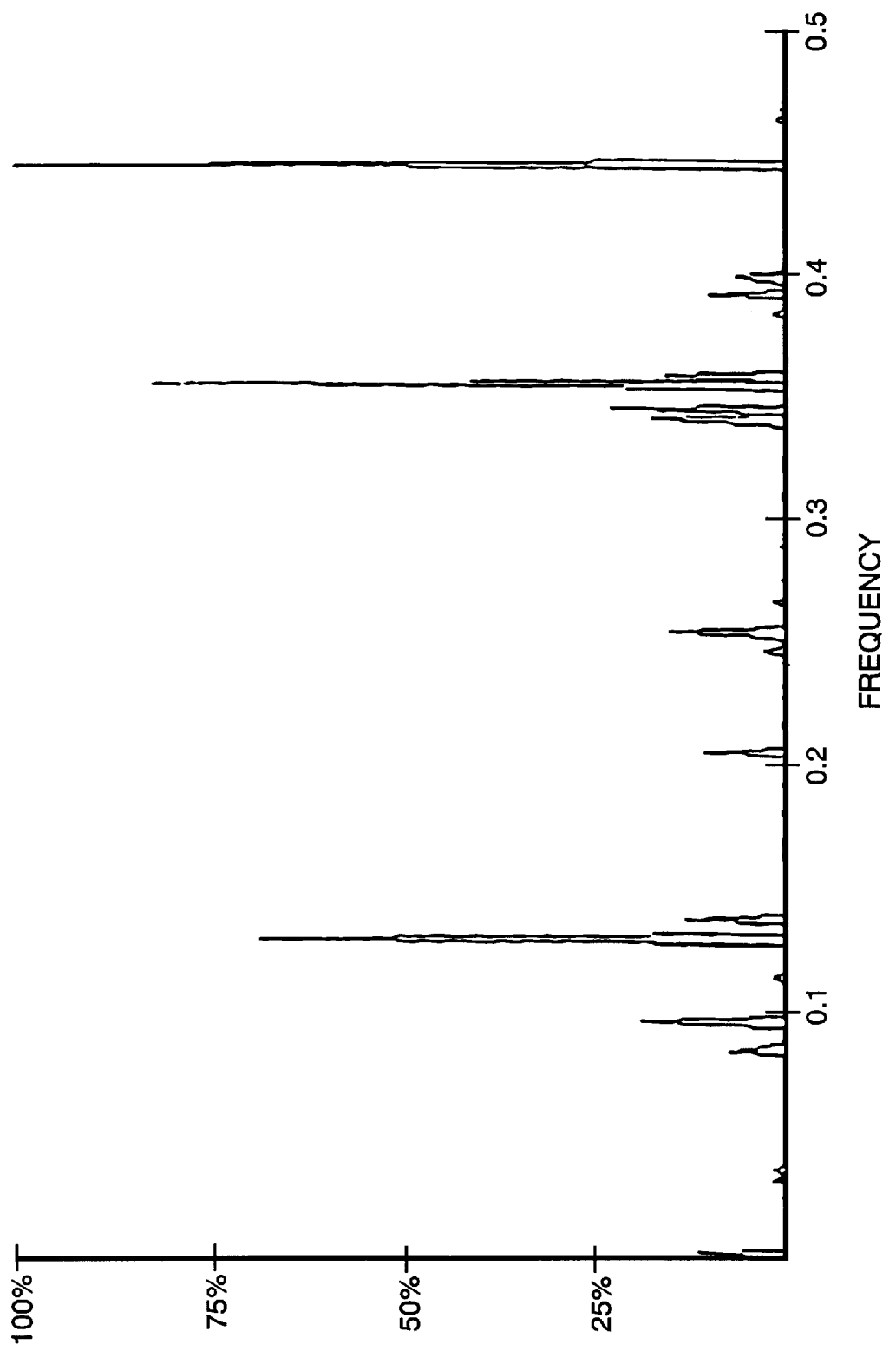
FIG. 3b represents the Fourier spectra of FLV protein.
Figure 3C:
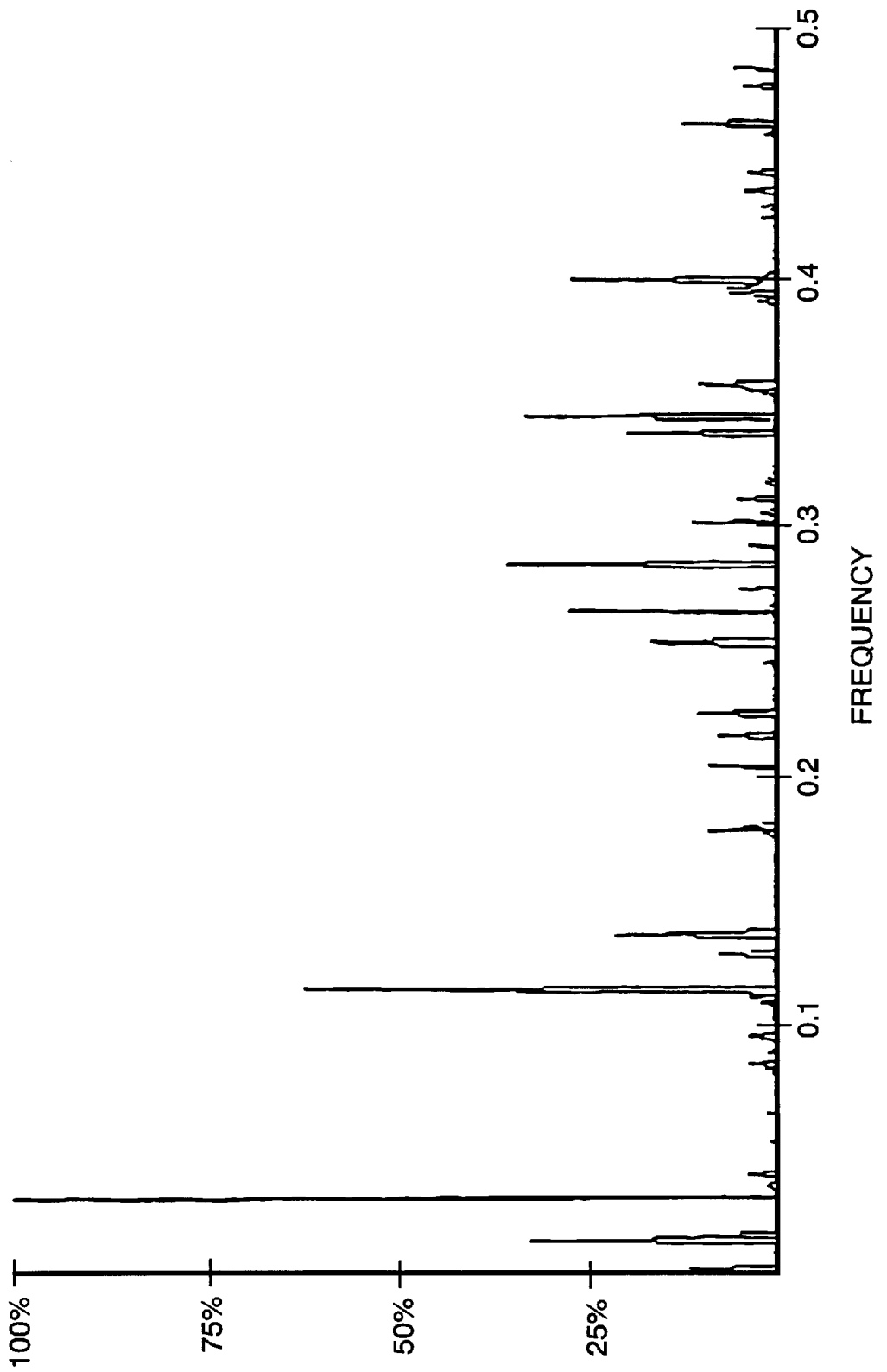
FIG. 3c represents the Fourier spectra of FLV protein.

It can be seen that the spike p15 (five isolates) has a characteristic frequency f=0.0137, FIG. 3(a), whilst the predominant characteristic frequency of the knob gp70 (six isolates) was f=0.4434, FIG. 3b, and the predominant characteristic frequency of the FLV envelop polyprotein (5 isolates) was f=0.0303, FIG. 3c.

Figure 3D:
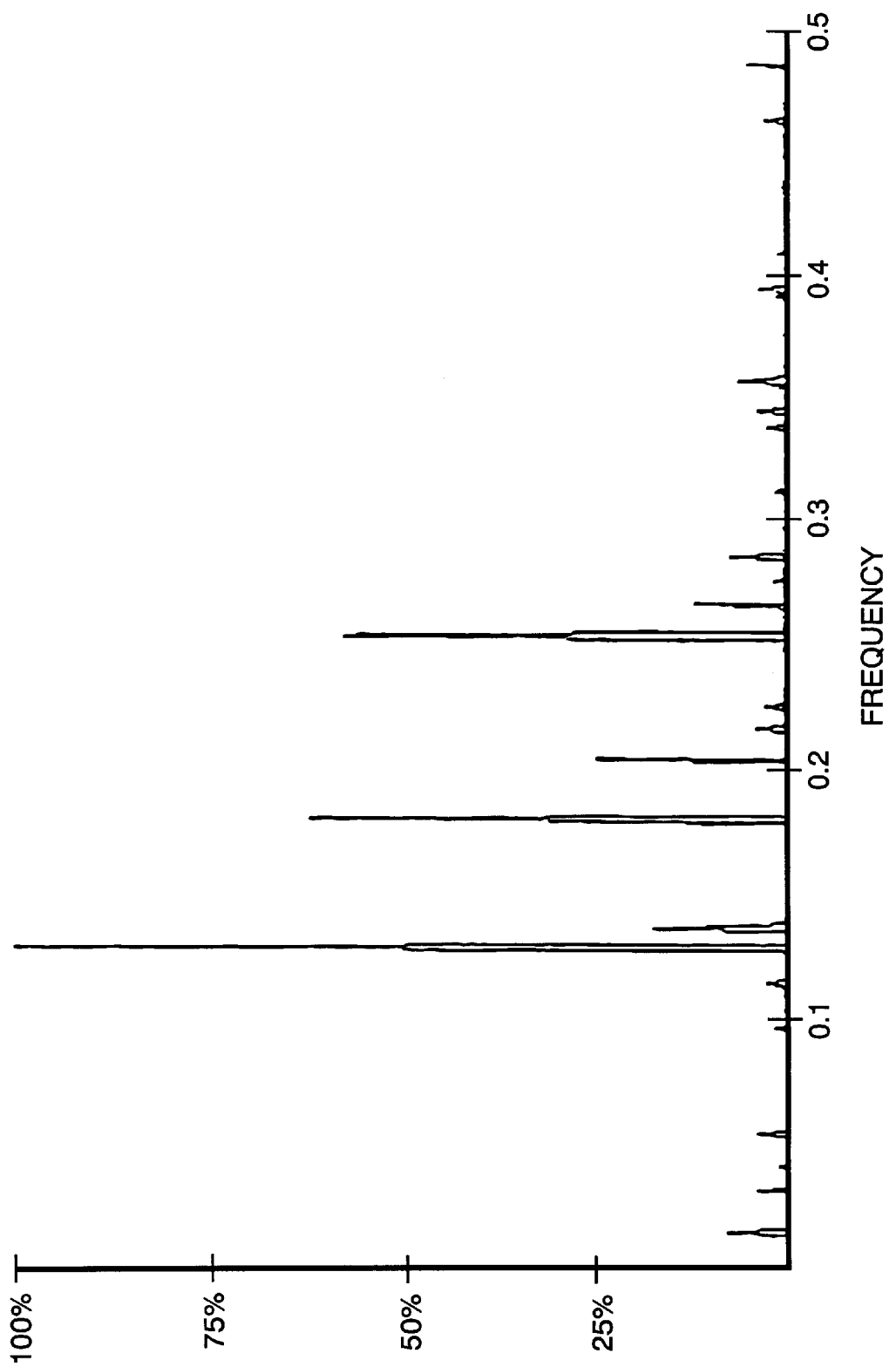
FIG. 3d represents the Fourier spectra of FLV protein.
Figure 3E:
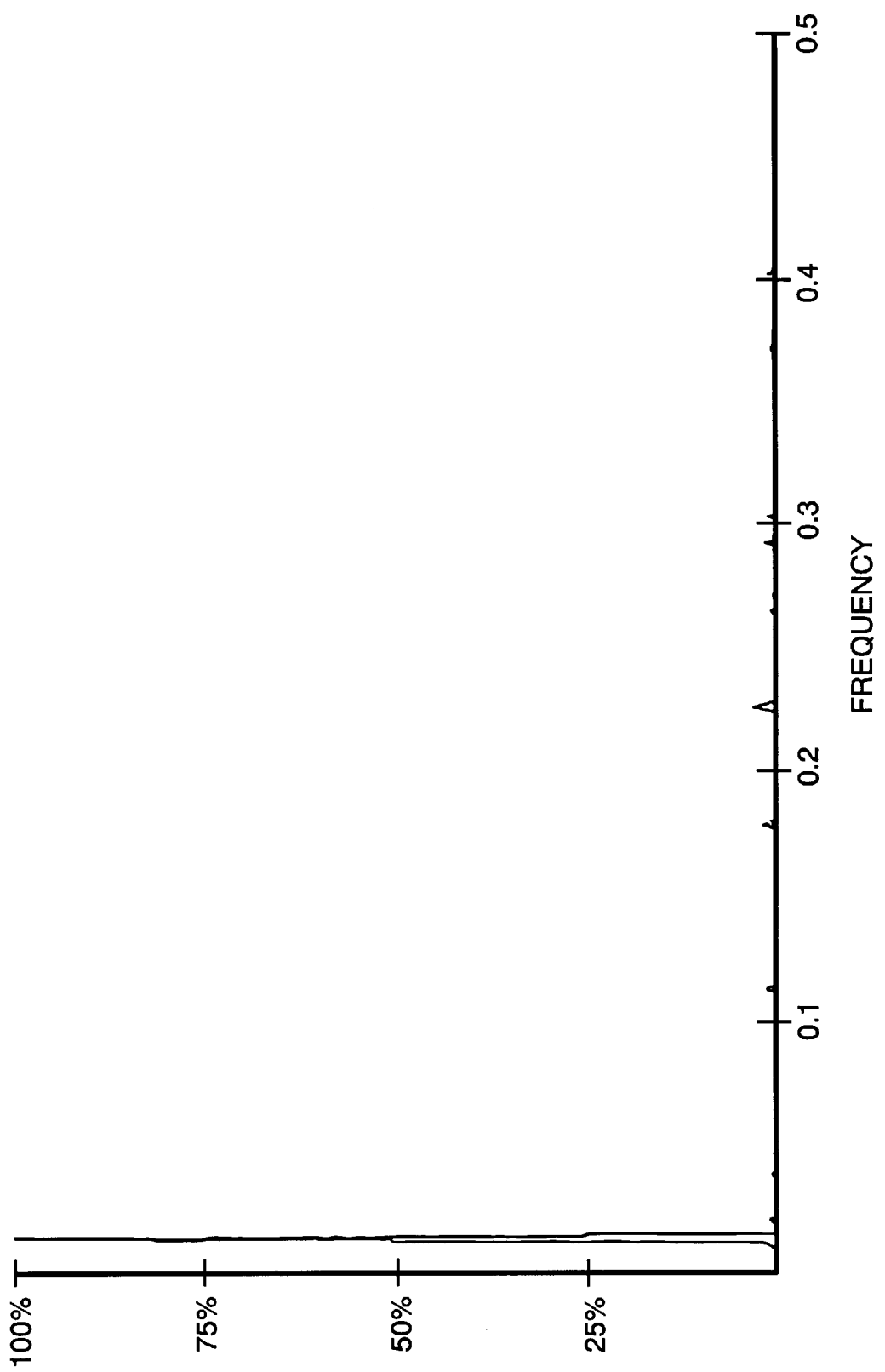
FIG. 3e represents the Fourier spectra of FLV protein.
Figure 3F:
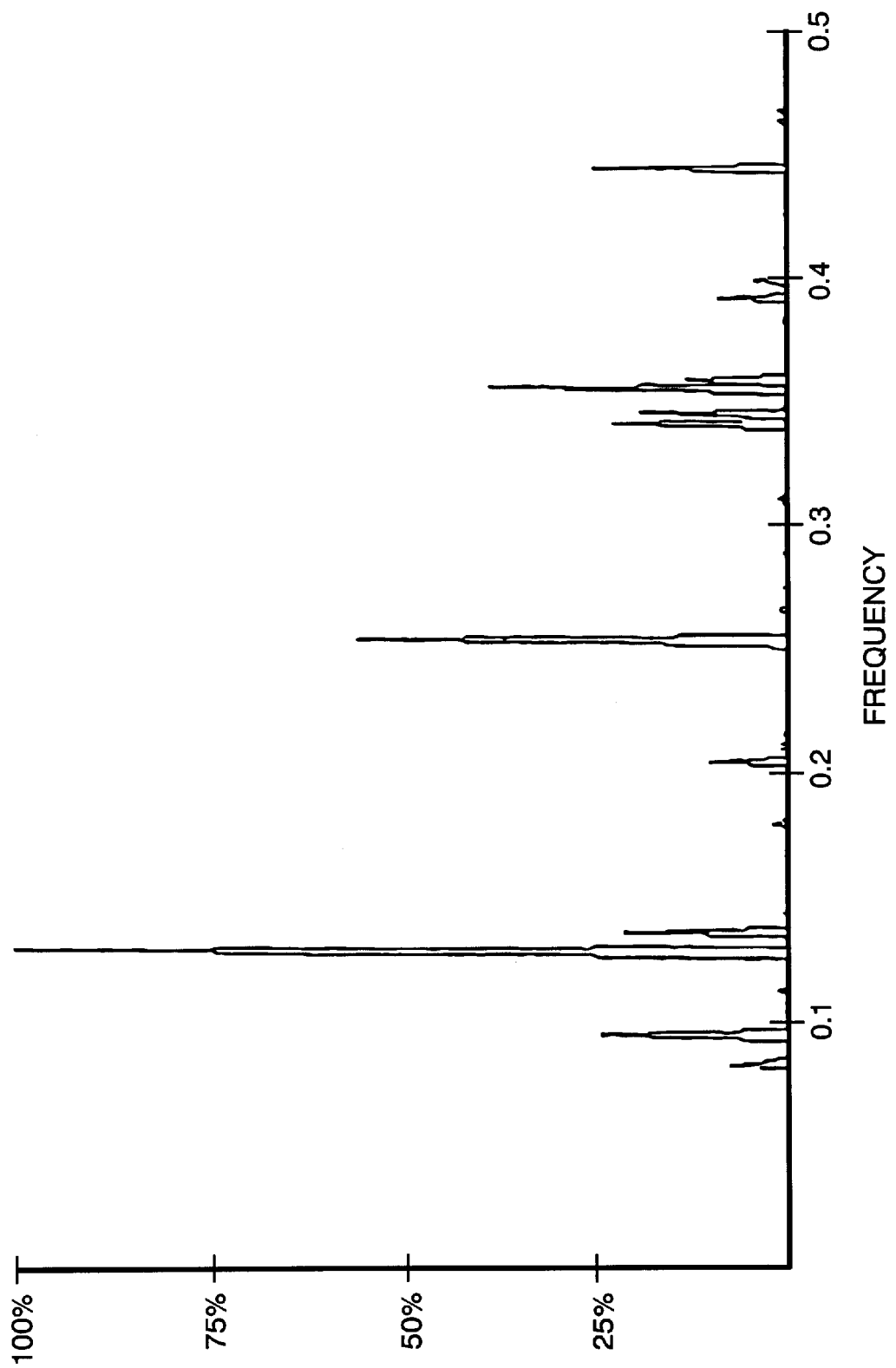
FIG. 3f represents the Fourier spectra of FLV protein.
Figure 4:
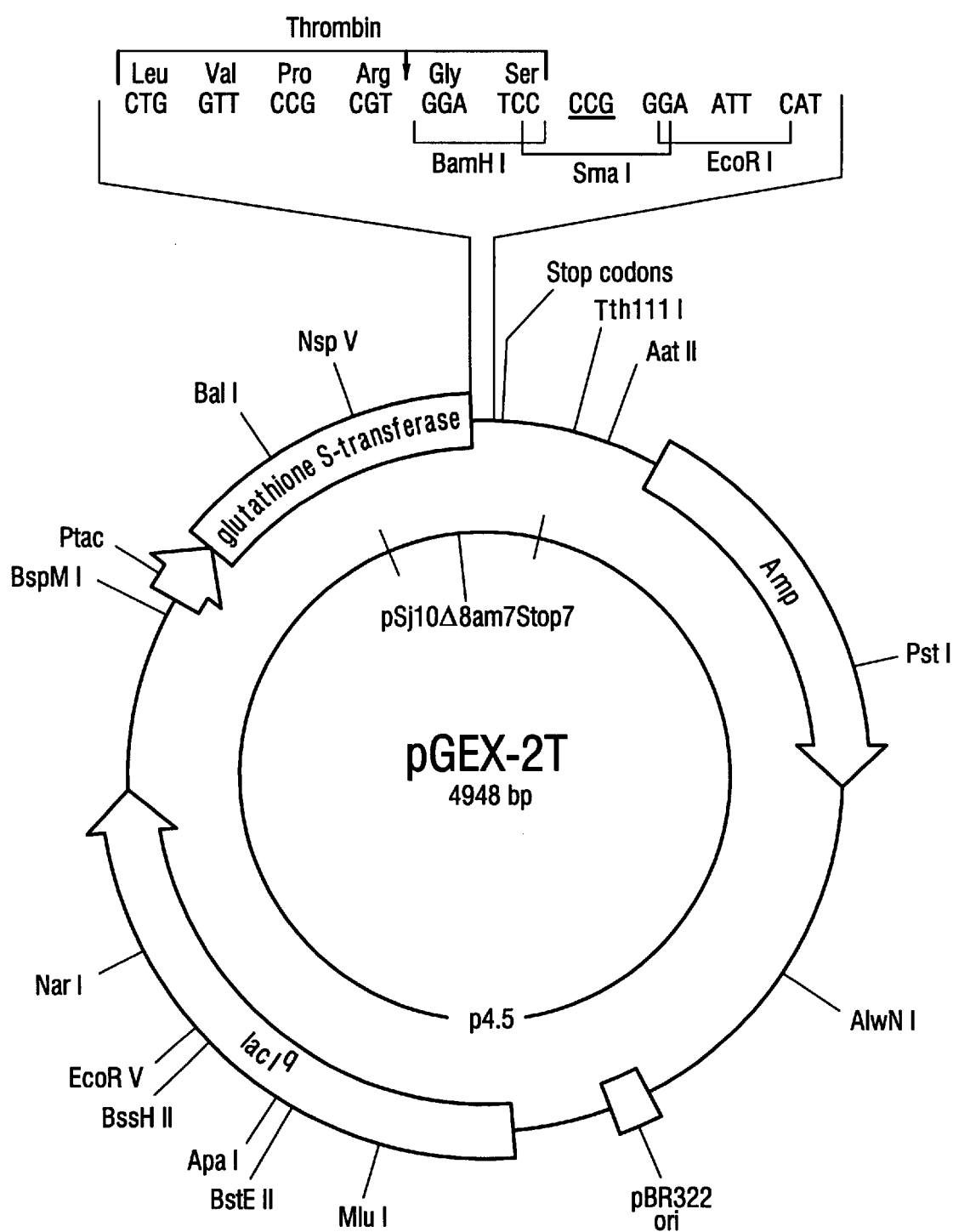
FIG. 4 represents the restriction map of plasmid pGEX-2.

In line with the concept that an increase in the amplitude of the characteristic frequency common to the retroviral polyprotein and its receptor will be evident from the multiple crossed spectral, a predominant characteristic frequency of f=0.1289 is observed for the FLV polyprotein envelop (5 isolates), the ENV fragment (3 isolates) and the T-cell receptor protein, FIG. 3d; a predominant characteristic frequency at f=0.0137 for the spike p15 protein (5 isolates) and the T-cell receptor protein, FIG. 3e; and a predominant characteristic frequency at f=0.1289 for the knob gp70 protein (6 isolates) and the T-cell receptor protein, (FIG. 3f).

Preparation of peptides immunologically related to FLV envelop proteins, knob-gp70 and spike 15.

Peptide FLV-kn20 corresponds, considering the characteristics of the moieties, to peptide knob-gp70. In other words, it has been found that it corresponds to a peptide of 20 amino-acids of the knob gp70 type with the sequence:

KDLRWHDIRW$^{10}$ HDIRWHDNRQ$^{20}$(SEQ ID NO:6)

Same sequence (f1=0.3984) and same phase as for knob-gp70 are found, associated with the recognition of spike p15.

Peptide FLV-knob 20 corresponds to a peptide having 20 amino acids of the anti-knob gp 70 type and has the sequence:

RNDHWRIDKW$^{10}$ RIDKWDLDKY$^{20}$(SEQ ID NO:7)

Its frequence is the same as the one observed with knob gp70 (f1=0.3984), but in inverse phase with knob gp70.

Peptide FLV-sp73 corresponds, with respect to the characteristics of the moieties, to spike 15, this is a peptide of 73 amino acids of the spike p15 type, having the sequence:

PPPEEGNNII$^{10}$ LIINNEEEPP$^{20}$ HHKKAYYWWQ$^{30}$

QQCTTRRRRD$^{40}$ DDDDDDDDDD$^{50}$ DDDDDDRRRR$^{60}$

TCMQQQWWYYA$^{70}$ KHH(SEQ ID NO:8)

Said peptide is in phase with spike p15 and has the same frequency ($f_2$=0.0137).

It will be noted that the sequence length is a direct consequence of the frequence low value.

Polypeptide FLV-spop 50 is in inverse phase with spike 15. This is a peptide of 50 amino acids of anti-spike 15 type, having the sequence:

RRRDDDDDDD$^{10}$ DDDDDDDDDR$^{20}$ RRRTCM-QQQW$^{30}$

WYYAKHHPPP$^{40}$ EEGNIIILII$^{50}$(SEQ ID NO:9)

Its frequence is the same as the one of protein spike 15 ($f_2$=0.0137), but in inverse phase with this protein. In this case also, the sequence length results in a frequence low value.

Peptide FLV-spkn 90 is a peptide of 90 amino acids of the protein spike p15 type and protein knob gp70.

Its sequence is as follows

AMPQKHQGWK$^{10}$ PWIYKEWGWA$^{20}$ PQPQWKT-KMQ$^{30}$

YRYRTWDWRR$^{40}$ QDQRRQDWFF$^{50}$ WRYQMKT-KWW$^{60}$

PQPAYEWEKY$^{70}$ IWEAYGQPKW$^{80}$ PMKWMKRWQR$^{90}$(SEQ ID NO:10)

This peptide is in phase with spike p15 and knob gp70, and has the same frequences (f1=0.3984 and f2=0.0137).

Peptide FLV-sp knob 50 is a peptide of 50 aminoacids, the characteristics of which correspond to a peptide of the anti-spike 15 type and anti-knob gp70.

Said peptide has the following sequence: FWDWTR-WDQR$^{10}$ DQDQRDWDQT$^{20}$ RWDWQRARYW$^{30}$ CHCAYQPQHK$^{40}$ WGWHHWLWPH50(SEQ ID NO:11)

It has the same frequencies as spike 15 and knob gp70, but these frequences are in inverse phase of the one of said both proteins.

EXAMPLE 6

Nucleotide fragments capable of coding for the artificial peptides related to HIV proteins and expression of these peptides.

Sequences Carrying the Coding Information for Peptides A1 and B1

Using classical techniques, one synthesises nucleotide sequences deduced from peptide sequences.

The cohesive termini on each side of the coding sequence are chosen in such a way as to carry the sites of restriction for BamH1 (5' terminus of a strand and 3' of the complementary strand) and EcoR1 (termini 3' and 5' of each strand, respectively) as follows:

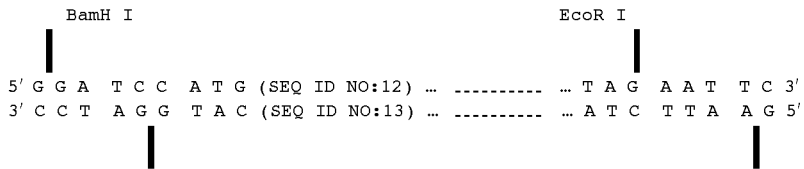

The nucleotide fragments obtained are indicated below with their complementary strand and the coded peptide sequence. The selected codons are among those the more frequently used in the case of genes highy expressed in E. coli (19). Several codons being capable of coding for a same amino acid, the nucleotidic sequences deduced from peptides A1 and B1 may respectively correspond to the following enchainments

Peptide A1

```
            K   Q   Q   Y   Y   W   Y   A   W   C   Q   P   P   Q   D   Q   L   I   M   D
            lys gln gln tyr tyr trp tyr ala trp cys gln pro pro gln asp gln leu ile met asp       (SEQ ID NO:2)
 cA1> 5'(+) GA TCC ATG AAA CAG CAG TAC TAC TGG TAC GCT TGG TGC CAG CCG CCG CAG GAC CAG CTG ATT ATG GAC TAG    (SEQ ID NO:17)
           [AAG CAA CAA TAT TAT GGC TGT CAA CAA CAA GTC GGC GTC CTG GTC GAC TAA TAC ATG ATG GAT]               (SEQ ID NO:18)
 cA1> 3'(-) G TAC TTT GTC GTC ATG ATG ACC ATG CGA ACC ACG GTC GGC CCG CCG GTC CTG GTC GAC TAA TAC CTG ATC TTA A 5' (SEQ ID NO:19)

K   Q   Q   Y   Y   W   Y   A   W   C   Q   P   P   Q   D   Q   L   I   M   D
            lys gln gln tyr tyr trp tyr ala trp cys gln pro pro gln asp gln leu ile met asp       (SEQ ID NO:2)
 cA11> 5'(+) GA TCC ATG AAG CAA CAA TAT TAT TGG TAT GCG TGG TGT CAA CCA CCA CAA GAT CAA CTC ATC ATG GAT TAG 3'  (SEQ ID NO:20)
 cA11> 3'(-) G TAC TTC GTT GTT ATA ATA ACC ATA CGC ACC ACA GTT GGT GGT GTT CTA GTT GAG TAG TAC CTA ATC TTA A 5' (SEQ ID NO:21)
```

Peptide B1

```
            D   D   A   L   Y   D   D   K   N   W   D   R   A   P   Q   R   C   Y   Y   Q
            asp asp ala leu tyr asp asp lys asn trp asp arg ala pro gln arg cys tyr tyr gln      (SEQ ID NO:4)
 cB1> 5'(+) GA TCC ATG GAC GAC GCT CTG TAC GAC GAC AAA AAC TGG GAC CGT GCT CCG CAG CGT TGC TAC TAC CAG TAG 3'  (SEQ ID NO:22)
           [GAT GAT GCG CTC TAT GAT GAT AAG AAT TGG GAT CGC GCG CCA CAA CGC TGT TAT TAT CAA]                   (SEQ ID NO:23)
 cB1> 3'(-) G TAC CTG CTG CGA GAC ATG CTG CTG TTT TTG ACC CTG GCA CGA GGC GTC GCA ACG ATG ATG GTC ATC TTA A 5' (SEQ ID NO:24)

D   D   A   L   Y   D   D   K   N   W   D   R   A   P   Q   R   C   Y   Y   Q
            asp asp ala leu tyr asp asp lys asn trp asp arg ala pro gln arg cys tyr tyr gln      (SEQ ID NO:4)
 cB11> 5'(+) GA TCC ATG GAT GAT GCG CTC TAT GAT GAT AAG AAT TGG GAT CGC GCG CCA CAA CGC TGT TAT TAT CAA TAG 3' (SEQ ID NO:25)
 cB11> 3'(-) G TAC CTA CTA CGC GAG ATA CTA CTA TTC TTA ACC CTA GCG CGC GGT GTT GCG ACA ATA ATA GTT ATC TTA A 5' (SEQ ID NO:26)
```

One should notice that the chain "+" represents the messenger RNA when the base T is replaced by the base U. In vivo, the messenger RNA is the result of transcription of the chain "−" (the complementary RNA of the chain "−").

Following are shown the complementary nucleotide sequences, used as coding sequences, and their corresponding peptide sequences cA1, cA11, cB1 and cB11.

Peptide CA1

```
                       V   H   N   Q   L   V   L   R   R   L   A   P   S   V   P   V   V   L   L   F
                      val his asn gln leu val leu arg arg leu ala pro ser val pro val val leu leu phe        (SEQ ID NO:16)
5'(+) GA TCC ATG GTC CAT AAT CAG CTG GTC CTG CGG CGG CTG GCA CCA AGC GTA CCA GTA GTA CTG CTG TTT TAG 3'     (SEQ ID NO:28)
      [GTT CAC AAC CAA CTC GTT CTC CGT CTC CGT CTC CCG TCT CTT CCG GTT GTT CCG GTT GTT CTC CTT TTC]          (SEQ ID NO:29)
3'(-)                                                                                                  G    (SEQ ID NO:30)
      TAC CAG GTA
      TTA GTC GAC
      CAG GAC GCC
      GCC GAC CGT
      GGT TCG CAT
      GCT CAT CAT
      GGT CAT CAT
      GAC GAC AAA
      ATC TTA A 5'
```

Peptide cA11

```
                       I   H   D   E   L   I   L   W   L   T   P   R   I   P   I   I   L   L   L
                      ile his asp glu leu ile leu trp leu thr pro arg ile pro ile ile leu leu leu           (SEQ ID NO:31)
5'(+) GA TCC ATG ATC CAT GAT GAG CTG ATC CTG TGG TTG ACA CCA CGC ATA CCA ATA ATA TTG CTT CTT TAG 3'         (SEQ ID NO:32)
      [ATT CAC GAC GAA CTG ACT CTG TGG CTG ACC CCG CGT ATC CCG ATC ATC ATC CTG CTG CTG]                     (SEQ ID NO:33)
3'(-) G TAC TAG GTA CTA CTC AAC TAG AAC ACC AAC TGT GGT GCG TAT TAT AAC GAA ATC TTA A 5'                    (SEQ ID NO:34)
```

Peptide cB1

```
                       L   V   V   A   T   L   R   S   T   V   P   V   F   V   V   V   Q   S   V   V
                      leu val val ala thr leu arg ser thr val pro val phe val val val gln ser val val      (SEQ ID NO:35)
5'(+) GA TCC ATG CTG GTA GTA GCA ACG CTG CGG AGC ACG GTC CCA GTC TTT GTC GTA CAG AGC GTC GTC TAG 3'         (SEQ ID NO:36)
      [CTC GTT GTT GCT ACT CTC CGT TCT ACT GTT CCG GTA TTC GTT GTT GTT CAG TCT GTT GTT]                     (SEQ ID NO:37)
3'(-) G TAC GAC CAT CAT CGT TGC GAC GCC TCG TGC CAG GGT CAG AAA CAG CAT GTC TCG CAG CAG ATC TTA A 5'        (SEQ ID NO:38)
```

Peptide cB11

```
                       L   I   I   T   A   L   W   R   A   I   P   I   L   I   I   E   R   I   I
                      leu ile ile thr ala leu trp arg ala ile pro ile leu ile ile glu arg ile ile          (SEQ ID NO:39)
5'(+) GA TCC ATG TTG ATA ATA ACA GCG TTG TGG CGC GCG ATC CCA ATT CTT ATC ATC GAG CGC ATC ATC TAG 3'         (SEQ ID NO:40)
```

-continued

3' (-)  [CTC ATC ATC ACC GCT CTG TGG CGT GCT ATT CCG ATC CTG ATT ATT ATC GAA CGT ATT ATT]  (SEQ ID NO:41)
G TAC AAC TAT TAT TGT CGC AAC ACC GCG CGC TAG CGC TAG GGT TAA GAA TAG TAG TAT CTC GCG TAG TAG ATC TTA A 5'  (SEQ ID NO:42)

The sequences of peptides A11 and B11, illustrated hereinafter, have been deduced from the complementary chains of those able to code for peptides cA1 and cB1 (mentioned inter brackets hereinabove)

Peptide A11

5' A ATT CTA GTT CAC AAC CAA CTC GTT CTC CGT CGT CTC GCT CCG TCT GTT CTC GTT CTC CTT TTC CAT G 3' (SEQ ID NO:43)
3' GAT CAA GTG TTG GTT GAG CAA GAG GCA GCA CGA GGC AGA CAA GAG CAA GAG GAA AAG GTA CCT AG 5' (SEQ ID NO:44)
COOH asn val val leu asn glu thr glu asn glu ser arg arg asn arg asn asn glu lys glu NH2
      N   V   V   L   N   E   T   E   N   E   S   R   R   N   R   N   N   E   K   E    (SEQ ID NO:45)

Peptide B11

5' A ATT CTA CTC GTT GCT ACT CTC CGT TCT ACT GTT CCG GTA TTC GTT GTT CAA TCT GTT CAT G 3' (SEQ ID NO:46)
3' GAT GAG CAA CGA TGA GAG GCA AGA TGA CAA GGC CAT AAG CAA CAA GTT AGA CAA GTA CCT AG 5' (SEQ ID NO:47)
COOH glu asn asn ser ser glu thr arg ser asn arg tyr glu asn asn leu arg asn asn NH2
      E   N   N   S   S   E   T   R   S   N   R   Y   E   N   N   L   R   N   N    (SEQ ID NO:48)

These nucleotide fragments are inserted in the plasmid pGEX-2T the restriction map of which is represented in FIG. 3, using the procedure of GST gene fusion from Pharmacia (Uppsala, Sweden).

The system has a promoter tac, an internal gene lac i7, and cleavage sites by thrombin.

The expressed peptide is fused at the carboxyl end of the glutathione S-transferase of *Schistosoma japonicum* and purified from bacterial lysates by affinity chromatography using a column of glutathione Sepharose 4B.

EXAMPLE 7

Study of immunological properties of pairs of artificial peptides.

production of antibodies using peptides of example 3.

Two month-old rabbits (New-Zealand) are immunised with the peptides obtained as described above. Rabbits are injected on day zero with 100 μg of peptides in complete Freund adjuvant. Then, every ten days, each rabbit is again administered with 100 μg of peptide in incomplete Freund adjuvant, with a total of at least 6 innoculations.

Sera are tested 3 days after the last injection using ELISA technique to determine the presence of antibodies against the inoculated peptide. The titres of the sera are expressed in logarithms of the highest dilution against which the serum shows a significant reactivity to an antigen.

Study of Cross Reactivities of Antibodies in ELISA Test

The various synthetic peptides to be analysed are coated on standard 96 well microtitre plates.

In each well are added 100 μl of a peptide solution at 1 μg/ml in PBS (phosphate buffer saline), pH7,4.

The free binding sites are blocked for approximately 14 hours at 4° C. with a solution of 1% (w/v) bovine serum albumin (BSA) in phosphate buffer, pH7.4. The plates are then washed extensively.

The serum of immunised rabbits and non-immunised rabbits are then added to the wells after dilution with a solution of PBS 0.01M, pH 7,4, NaCl 0.15 M, BSA 1% and Tween 20 0.1%, then the plates are incubated for one hour at 37° C.

After several washes, one adds anti-rabbit goat IgG antiserum conjugated to horseradish peroxydase (dilution 1/1000), then the plates are further incubated for one hour at 37° C.

The enzymatic activity is determined by using o-phenylene-diamine as substrate. Absorbance is measured at 492 nm.

The results obtained are shown in table 2:

TABLE 2

|  | Anti-A1 | Anti-A2 | Anti-B1 | Anti-B2 |
| --- | --- | --- | --- | --- |
| A1 | 5.1 | 3.3 | 2.4 | 0.9 |
| A2 | 3.6 | 5.1 | 2.1 | 2.7 |
| B1 | 0 | 0 | 3.6 | 2.4 |
| B2 | 0.9 | 3.6 | 3.9 | 5.4 |
| gp120 | 1.5 | 1.2 | 5.4 | 1.8 |

The values represent the logarithms of the highest dilutions against which the serum shows significant reactivity.

The results show that the animals immunised with peptide A1 produce polyclonal antibodies which crossreact with peptide A2 and that, on the other hand, the animals immunised with peptide A2 produce antibodies which crossreact with peptide A1.

These results show the cross reactivity of anti-A1 and anti-A2 sera directed against peptides A1 and A2 respectively, which are not homologous as far as their structure is concerned but have in common the frequency f1 and are of the same phase.

The cross recognition of anti-A1 and anti-A2 sera with peptides A2 and A1, respectively, thus does appear to be associated with frequency f1.

Peptides A1 and A2 are only weakly recognised by rabbit anti-B1 polyclonal antibodies by ELISA test.

Peptide B2, which presents the same phase as peptide B1 with characteristic frequency f1=0.1855, crossreacts with anti-B1 serum, and the polyclonal antibodies of serum directed against peptide B2 recognise peptide B1 and form a complex of the type antigen-antibody.

Therefore, the specificity of cross reactivity of anti-B1 and anti-B2 sera is in agreement with the idea of a common frequency f1 for the two peptides B1 and B2, as demonstrated above with the cross reactivity of anti-A1 and anti-A2 sera with peptides A2 and A1 respectively. Serum anti-A1 does not markedly crossreact with peptides B1 or B2 which have opposite phases, this parameter being therefore also involved in biomolecular recognition. Similarly, anti-B2 serum does not cross react with peptide A1.

Anti-B2 serum crossreacts weakly with peptide A2, while polyclonal antibodies of anti-A2 serum recognise significantly peptide B2 in the ELISA assays. This cross reactivity can be attributed to the homology of sequences A2 and B2 which have two fragments in common, that is to say DFHIWDDYLKRD(SEQ ID NO:14) and QEPMDFHI (SEQ ID NO:15), even though the position of the sequences is inversed.

Similarly, no cross reactivity is observed between peptide B1 and anti-A1 and anti-A2 sera, peptide B1 presenting the inverse phase to the common frequency (frequencies) with peptides A1 and A2.

Finally, serum anti-B1 recognises HIV-1 gp120 recombinant glycoprotein (Baculovirus), while sera anti-A1, anti-A2 and anti-B2 do not crossreact with gp120 in the experimental conditions.

EXAMPLE 8

Study of the Reactivity of Sera with HIV Proteins in the Immunoblot Test

Figure 5:
FIG. 5 represents the immunoblot picture illustrating the reaction of proteins of HIV-1 with an antibody directed against an artificial peptide of the invention.

Reported below are the results obtained with a rabbit anti-B1 serum using a commercially available immunoblot kit, such as that produced by Diagnostic Pasteur containing HIV-1 proteins of LAVbru. The serum is diluted and incubated with immunoblot strips with goat anti-rabbit IgG labelled with alkaline phosphatase. The strips are developed using a system with phosphatase substrate (Diagnostic Pasteur). The results obtained are shown in FIG. 5.

The figure shows that the antibodies induced by peptide B1 and present in the anti-B1 serum are capable of reacting with several HIV-1 proteins. Indeed, the antibodies of that serum have been taken up by the protein POL p68 (coded by the gene of the reversed transcriptase of the virus), by the protein GAG p55 (precursor of GAG proteins), as well as by proteins derived from that precursorr: p18, p24/25 and p40. Similarly, the compound showing a sharp band at 43 kDa, localised in the region corresponding to the defused bands of gp41, also crossreacts.

Protein p15 is the only protein among the GAG proteins which is not recognised by the anti-B1 serum. Finally, binding of anti-B1 antibodies to gp120 does not significantly appears in the Immunoblot test.

The recognition of several HIV proteins (of which those derived from genes POL and GAG) by the anti-B1 antibodies is confirmed by using HIV-1 IgG Western blot kit available from Ortho Diagnostic Systems.

The experiments using recombinant Baculovirus gp120 show that the anti-B1 serum reacts significantly with that protein of the envelop (ELISA).

Moreover, several HIV-1 proteins have been immunoprecipitated by antibodies of anti-B1 serum, including gp160 and gp120.

The gene containing the information for peptide B1 has been synthesized and inserted in plasmid pGEX-2T (as disclosed in example 7) and then introduced in the bacteria. Among the bacterial proteins, the presence of peptide B1 (fused to S-transferase glutathione) is revealed by anti-B1 serum using an immunoblot, after migration of the proteins on an electrophoresis gel and their transfer on nitrocellulose.

EXAMPLE 9

Lymphocyte Growth Stimulation Test

Rabbits were immunized by peptide cA1 the sequence of which is as follows: VHNQLVLRRLAPSVPVVLLF (SEQ ID NO:27)

It will be recalled that peptide cA1 belongs to peptides B group, since its amino acid enchainment was deduced from the nucleotide sequence complementary to the one of peptide A1, this last one belonging to group A (as disclosed in example 5).

The protocol is as follows:

1) immunization of rabbits

300 μg of peptides were administered to rabbits by ID or SC injection with Freund adjuvant (complete and incomplete).

One injection is done every 10 days, a minimum of 8 injections being done.

The antibody level is determined using Elisa method, one week after the last injection.

2) lymphocyte recovering

Samplings were done on immunized rabbit ears (20 ml of blood are necessary). The same sampling was done on a control rabbit (non immunized).

One volume of whole blood was diluted into two volumes of Hanks solution, then placed on a Ficoll buffy coat and centrifuged at 1300 t/min during 30 min.

The lymphocytar anneal was taken up, then rinsed two times in Hanks solution, and resuspended in 1 ml of RPMI 1640 medium.

The lymphocytes were then counted on Mallassez cell, then the number was adjusted to have at least 250 000 cells/well.

3) Culture

The culture was carried out on 96 well plates with flat bottom, treated for cellular culture (Falcon n° 3072).

The culture medium was RPMI 1640 with antibiotics, glutamine and 10% of said rabbit serum, taken up before immunization and decomplemented.

Each well received 250 000 cells and increase amounts of immunogen peptide (10 to 75 μg/well).

The plates were put in an incubator at 37° C. containing 5% of $CO_2$ during 5 days.

4) Incorporation of tritiated thymidine

At day 5, 1 μCi of 3H thymidine was incorporated by well.

5) Harvest and counting of the incorporated radioactivity

After one night incubation (15 hours), the well content was harvested on glass fiber filters using a sucking collector, filters were then dried, counted in a scintillating liquid.

It was shown by the experiences that the lymphocyte proliferation of animals immunized with peptide cA1 was stimulated in the presence of said peptide as well as in the presence of HIV-1 gp120 glycoprotein. Moreover, a significant stimulation of the same lymphocytes by peptide B1 was noticed.

References:

1. Hay, F. C. et al, (1984), pp 117–138. Academic Press, Inc., Orlando, Fla.
2. Finberg, R. W. et al (1987), pp 7–11. Cold Spring Harbor Laboratory, Cold Spring Harbor, N.Y.
3. Cosic, I., et al (1991) Eur. J. Biochem. 198, 113–119.
4. Veljkovic, V. et al I. (1972) Physical Review Letters, 29, 105–108.
5. Heine, V., et al (1973) MIR, Moscow.
6. Rabiner, L. et al, (1975). Prentice-Hall, London.
7. Lasky, L. A. et al, Cell, 50, 673–678.
8. Houghten, R. A. (1985) Proc. Natl. Acad. Sci. USA, 82, 5131–5135.
9. Houghten, R. A. et al (1986) Int. J. Peptide Protein Res., 27, 673–678.
10. Riedel et al (1986), J. Virol. 60, 242–250.
11. Nunberg et al, (1984), J. Virol. 49, 629–632.
12. Stewart et al, (1986), J. Virol. 58, 825–834.
13. Nicolaisen-Strouss et al, (1987), J. Virol., 61, 3410–3415.
14. Kumar et al, (1989), J. Virol. 63, 2379–2384.
15. Elder et al, (1987), J. Virol 61, 8–15.
16. Malik et al, (1988), J. Gen Virol. 69, 1695–1710.
17. Shimotohno et al, (1985), PNAS 82, 3101–3105.
18. Sonigo et al, (1985), Cell, 42, 369–382.
19. Sunnarborg et al, (1990) 172, 2642–2649.

What is claimed is:
1. A peptide consisting of SEQ ID NO: 1.
2. A peptide consisting of SEQ ID NO: 2.
3. A peptide consisting of SEQ ID NO: 3.
4. A peptide consisting of SEQ ID NO: 4.
5. A peptide consisting of SEQ ID NO: 5.
6. A peptide consisting of SEQ ID NO: 27.

* * * * *

SEQUENCE LISTING (1) GENERAL INFORMATION:

(iii) NUMBER OF SEQUENCES: 48

(2) INFORMATION FOR SEQ ID NO: 1:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..44

(xi) SEQUENCE DESCRIPTION: SEQ ID NO: 1:

Thr Ile Thr Leu Pro Cys Arg Ile Lys Gln Phe Ile Asn Met Trp Gln
1               5                   10                  15

Glu Val Gly Lys Ala Met Tyr Ala Pro Pro Ile Ser Gly Gln Ile Arg
                20                  25                  30

Cys Ser Ser Asn Ile Thr Gly Leu Leu Leu Thr Arg
            35                  40

(2) INFORMATION FOR SEQ ID NO: 2:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 2:

Lys Gln Gln Tyr Tyr Trp Tyr Ala Trp Cys Gln Pro Pro Gln Asp Gln
1               5                   10                  15

Leu Ile Met Asp
            20

(2) INFORMATION FOR SEQ ID NO: 3:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 3:

Leu Lys Arg Asp Gln Glu Pro Met Asp Phe His Ile Trp Asp Asp Tyr
1               5                   10                  15

Leu Lys Arg Asp
            20

(2) INFORMATION FOR SEQ ID NO: 4:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 4:

Asp Asp Ala Leu Tyr Asp Asp Lys Asn Trp Asp Arg Ala Pro Gln Arg
1               5                   10                  15

Cys Tyr Tyr Gln
            20

(2) INFORMATION FOR SEQ ID NO: 5:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 5:

Asp Phe His Ile Trp Asp Asp Tyr Leu Lys Arg Asp Gln Glu Pro Met
1               5                   10                  15

Asp Phe His Ile
            20

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 6:

Lys Asp Leu Arg Trp His Asp Ile Arg Trp His Asp Ile Arg Trp His
1               5                   10                  15

Asp Asn Arg Gln
            20

(2) INFORMATION FOR SEQ ID NO: 7:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 7:

Arg Asn Asp His Trp Arg Ile Asp Lys Trp Arg Ile Asp Lys Trp Asp
1               5                   10                  15

Leu Asp Lys Tyr
            20

(2) INFORMATION FOR SEQ ID NO: 8:

(i) SEQUENCE CHARACTERISTICS:
        (A) LENGTH: 73 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..73

(xi) SEQUENCE DESCRIPTION: SEQ ID NO: 8:

Pro Pro Pro Glu Glu Gly Asn Asn Ile Ile Leu Ile Ile Asn Asn Glu
1               5                   10                  15

Glu Glu Pro Pro His His Lys Lys Ala Tyr Tyr Trp Trp Gln Gln Gln
            20                  25                  30

Cys Thr Thr Arg Arg Arg Arg Asp Asp Asp Asp Asp Asp Asp Asp Asp
            35                  40                  45

Asp Asp Asp Asp Asp Asp Asp Arg Arg Arg Thr Cys Met Gln Gln
    50                  55                  60

Gln Trp Trp Tyr Tyr Ala Lys His His
65              70

(2) INFORMATION FOR SEQ ID NO: 9:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..50

(xi) SEQUENCE DESCRIPTION: SEQ ID NO: 9:

Arg Arg Arg Asp Asp Asp Asp Asp Asp Asp Asp Asp Asp Asp Asp
1               5                   10                  15

Asp Asp Asp Arg Arg Arg Arg Thr Cys Met Gln Gln Gln Trp Trp Tyr
            20                  25                  30

Tyr Ala Lys His His Pro Pro Pro Glu Glu Gly Asn Ile Ile Ile Leu
            35                  40                  45

Ile Ile
50

(2) INFORMATION FOR SEQ ID NO: 10:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..90

(xi) SEQUENCE DESCRIPTION: SEQ ID NO: 10:

Ala Met Pro Gln Lys His Gln Gly Trp Lys Pro Trp Ile Tyr Lys Glu
1               5                   10                  15

Trp Gly Trp Ala Pro Gln Pro Gln Trp Lys Thr Lys Met Gln Tyr Arg
            20                  25                  30

Tyr Arg Thr Trp Asp Trp Arg Arg Gln Asp Gln Arg Arg Gln Asp Trp
            35                  40                  45

Phe Phe Trp Arg Tyr Gln Met Lys Thr Lys Trp Trp Pro Gln Pro Ala
    50                  55                  60

Tyr Glu Trp Glu Lys Tyr Ile Trp Glu Ala Tyr Gly Gln Pro Lys Trp
65              70                  75                  80

Pro Met Lys Trp Met Lys Arg Trp Gln Arg
            85                  90

(2) INFORMATION FOR SEQ ID NO: 11:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..50

(xi) SEQUENCE DESCRIPTION: SEQ ID NO: 11:

```
Phe Trp Asp Trp Thr Arg Trp Asp Gln Arg Asp Gln Asp Gln Arg Asp
1               5                   10                  15

Trp Asp Gln Thr Arg Trp Asp Trp Gln Arg Ala Arg Tyr Trp Cys His
            20                  25                  30

Cys Ala Tyr Gln Pro Gln His Lys Trp Gly Trp His His Trp Leu Trp
            35                  40                  45

Pro His
    50
```

(2) INFORMATION FOR SEQ ID NO: 12:

(i) SEQUENCE CHARACTERISTICS:
        (A) LENGTH: 9 base pairs
        (B) TYPE: nucleic acid
        (C) STRANDEDNESS: double
        (D) TOPOLOGY: linear (ii) MOLECULE TYPE: genomic DNA (iii) HYPOTHETICAL: YES (ix) FEATURE:
        (A) NAME/KEY: misc_RNA
        (B) LOCATION: 1..9

(xi) SEQUENCE DESCRIPTION: SEQ ID NO: 12:

```
GGATCCATG                                                       9
```

(2) INFORMATION FOR SEQ ID NO: 13:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: genomic DNA (iii) HYPOTHETICAL: YES (ix) FEATURE:
        (A) NAME/KEY: misc_RNA
        (B) LOCATION: 1..8

(xi) SEQUENCE DESCRIPTION: SEQ ID NO: 13:

```
TAGAATTC                                                        8
```

(2) INFORMATION FOR SEQ ID NO: 14:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
            (A) NAME/KEY: Peptide
            (B) LOCATION: 1..12

(xi) SEQUENCE DESCRIPTION: SEQ ID NO: 14:

Asp Phe His Ile Trp Asp Asp Tyr Leu Lys Arg Asp
1               5                   10

(2) INFORMATION FOR SEQ ID NO: 15:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO: 15:

Gln Glu Pro Met Asp Phe His Ile
1               5

(2) INFORMATION FOR SEQ ID NO: 16:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 16:

Val His Asn Gln Leu Val Leu Arg Arg Leu Ala Pro Ser Val Pro Val
1               5                   10                  15

Val Leu Leu Phe
            20

(2) INFORMATION FOR SEQ ID NO: 17:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: CDS
        (B) LOCATION: 3..71

(xi) SEQUENCE DESCRIPTION: SEQ ID NO: 17:

GATCCATGAA ACAGCAGTAC TACTGGTACG CTTGGTGCCA GCCGCCGCAG GACCAGCTGA      60

TTATGGACTA G                                                          71

(2) INFORMATION FOR SEQ ID NO: 18:

(i) SEQUENCE CHARACTERISTICS:
        (A) LENGTH: 60 base pairs (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: CDS
        (B) LOCATION: 1..60

(xi) SEQUENCE DESCRIPTION: SEQ ID NO: 18:

AAGCAACAAT ATTATTGGTA TGCGTGGTGT CAACCACCAC AAGATCAACT CATCATGGAT     60

(2) INFORMATION FOR SEQ ID NO: 19:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: YES (ix) FEATURE:
        (A) NAME/KEY: CDS
        (B) LOCATION: 2..70

(xi) SEQUENCE DESCRIPTION: SEQ ID NO: 19:

AATTCTAGTC CATAATCAGC TGGTCCTGCG GCGGCTGGCA CCAAGCGTAC CAGTAGTACT     60

GCTGTTTCAT G                                                         71

(2) INFORMATION FOR SEQ ID NO: 20:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: YES (ix) FEATURE:
        (A) NAME/KEY: CDS
        (B) LOCATION: 3..71

(xi) SEQUENCE DESCRIPTION: SEQ ID NO: 20:

GATCCATGAA GCAACAATAT TATTGGTATG CGTGGTGTCA ACCACCACAA GATCAACTCA     60

TCATGGATTA G                                                         71

(2) INFORMATION FOR SEQ ID NO: 21:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: YES (ix) FEATURE:
            (A) NAME/KEY: CDS
            (B) LOCATION: 2..70

(xi) SEQUENCE DESCRIPTION: SEQ ID NO: 21:

AATTCTAATC CATGATGAGT TGATCTTGTG GTGGTTGACA CCACGCATAC CAATAATATT     60

GTTGCTTCAT G                                                         71

(2) INFORMATION FOR SEQ ID NO: 22:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: CDS
            (B) LOCATION: 3..71

(xi) SEQUENCE DESCRIPTION: SEQ ID NO: 22:

GATCCATGGA CGACGCTCTG TACGACGACA AAAACTGGGA CCGTGCTCCG CAGCGTTGCT     60

ACTACCAGTA G                                                         71

(2) INFORMATION FOR SEQ ID NO: 23:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: CDS
            (B) LOCATION: 1..60

(xi) SEQUENCE DESCRIPTION: SEQ ID NO: 23:

GATGATGCGC TCTATGATGA TAAGAATTGG GATCGCGCGC CACAACGCTG TTATTATCAA     60

(2) INFORMATION FOR SEQ ID NO: 24:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (iv) ANTI-SENSE: YES (ix) FEATURE:
            (A) NAME/KEY: CDS
            (B) LOCATION: 2..70

(xi) SEQUENCE DESCRIPTION: SEQ ID NO: 24:

AATTCTACTG GTAGTAGCAA CGCTGCGGAG CACGGTCCCA GTTTTTGTCG TCGTACAGAG     60

CGTCGTCCAT G                                                            71

(2) INFORMATION FOR SEQ ID NO: 25:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: NO (ix) FEATURE:
        (A) NAME/KEY: CDS
        (B) LOCATION: 3..71

(xi) SEQUENCE DESCRIPTION: SEQ ID NO: 25:

GATCCATGGA TGATGCGCTC TATGATGATA AGAATTGGGA TCGCGCGCCA CAACGCTGTT    60

ATTATCAATA G                                                            71

(2) INFORMATION FOR SEQ ID NO: 26:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: YES (ix) FEATURE:
        (A) NAME/KEY: CDS
        (B) LOCATION: 2..70

(xi) SEQUENCE DESCRIPTION: SEQ ID NO: 26:

AATTCTATTG ATAATAACAG CGTTGTGGCG CGCGATCCCA ATTCTTATCA TCATAGAGCG    60

CATCATCCAT G                                                            71

(2) INFORMATION FOR SEQ ID NO: 27:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 27:

Val His Asn Gln Leu Val Leu Arg Arg Leu Ala Pro Ser Val Pro Val
 1               5                  10                  15

Val Leu Leu Phe
            20

(2) INFORMATION FOR SEQ ID NO: 28:

(i) SEQUENCE CHARACTERISTICS:
        (A) LENGTH: 71 base pairs (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: NO (ix) FEATURE:
        (A) NAME/KEY: CDS
        (B) LOCATION: 3..71

(xi) SEQUENCE DESCRIPTION: SEQ ID NO: 28:

GATCCATGGT CCATAATCAG CTGGTCCTGC GGCGGCTGGC ACCAAGCGTA CCAGTAGTAC    60

TGCTGTTTTA G                                                       71

(2) INFORMATION FOR SEQ ID NO: 29:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: NO (ix) FEATURE:
        (A) NAME/KEY: CDS
        (B) LOCATION: 1..60

(xi) SEQUENCE DESCRIPTION: SEQ ID NO: 29:

GTTCACAACC AACTCGTTCT CCGTCGTCTC GCTCCGTCTG TTCCGGTTGT TCTCCTTTTC    60

(2) INFORMATION FOR SEQ ID NO: 30:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (xi) SEQUENCE DESCRIPTION: SEQ ID NO: 30:

AATTCTAAAA CAGCAGTACT ACTGGTACGC TTGGTGCCAG CCGCCGCAGG ACCAGCTGAT    60

TATGGACCAT G                                                       71

(2) INFORMATION FOR SEQ ID NO: 31:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 31:

Ile His Asp Glu Leu Ile Leu Trp Trp Leu Thr Pro Arg Ile Pro Ile

```
            1               5              10              15
Ile Leu Leu Leu
            20
```

(2) INFORMATION FOR SEQ ID NO: 32:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: CDS
        (B) LOCATION: 3..71

(xi) SEQUENCE DESCRIPTION: SEQ ID NO: 32:

```
GATCCATGAT CCATGATGAG TTGATCTTGT GGTGGTTGAC ACCACGCATA CCAATAATAT    60

TGTTGCTTTA G                                                        71
```

(2) INFORMATION FOR SEQ ID NO: 33:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: misc_RNA
        (B) LOCATION: 1..60

(xi) SEQUENCE DESCRIPTION: SEQ ID NO: 33:

```
ATTCACGACG AACTGATTCT GTGGTGGCTG ACCCCGCGTA TCCCGATCAT CCTGCTGCTG    60
```

(2) INFORMATION FOR SEQ ID NO: 34:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: CDS
        (B) LOCATION: 2..70

(xi) SEQUENCE DESCRIPTION: SEQ ID NO: 34:

```
AATTCTAAAG CAACAATATT ATTGGTATGC GTGGTGTCAA CCACCACAAG ATCAACTCAT    60

CATGGATCAT G                                                        71
```

(2) INFORMATION FOR SEQ ID NO: 35:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
            (A) NAME/KEY: Peptide
            (B) LOCATION: 1..20

(xi) SEQUENCE DESCRIPTION: SEQ ID NO: 35:

Leu Val Val Ala Thr Leu Arg Ser Thr Val Pro Val Phe Val Val Val
 1               5                  10                  15

Gln Ser Val Val
            20

(2) INFORMATION FOR SEQ ID NO: 36:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: CDS
            (B) LOCATION: 3..71

(xi) SEQUENCE DESCRIPTION: SEQ ID NO: 36:

GATCCATGCT GGTAGTAGCA ACGCTGCGGA GCACGGTCCC AGTTTTTGTC GTCGTACAGA      60

GCGTCGTCTA G                                                          71

(2) INFORMATION FOR SEQ ID NO: 37:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: misc_RNA
            (B) LOCATION: 1..60

(xi) SEQUENCE DESCRIPTION: SEQ ID NO: 37:

CTCGTTGTTG CTACTCTCCG TTCTACTGTT CCGGTATTCG TTGTTGTTCA ATCTGTTGTT      60

(2) INFORMATION FOR SEQ ID NO: 38:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: CDS
            (B) LOCATION: 2..70

(xi) SEQUENCE DESCRIPTION: SEQ ID NO: 38:

AATTCTAGAC GACGCTCTGT ACGACGACAA AAACTGGGAC CGTGCTCCGC AGCGTTGCTA      60

```
CTACCAGCAT G                                                          71

(2) INFORMATION FOR SEQ ID NO: 39:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..20

(xi) SEQUENCE DESCRIPTION: SEQ ID NO: 39:

Leu Ile Ile Thr Ala Leu Trp Arg Ala Ile Pro Ile Leu Ile Ile Ile
 1               5                  10                  15

Glu Arg Ile Ile
            20

(2) INFORMATION FOR SEQ ID NO: 40:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: CDS
        (B) LOCATION: 3..71

(xi) SEQUENCE DESCRIPTION: SEQ ID NO: 40:

GATCCATGTT GATAATAACA GCGTTGTGGC GCGCGATCCC AATTCTTATC ATCATAGAGC      60

GCATCATCTA G                                                          71

(2) INFORMATION FOR SEQ ID NO: 41:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (ix) FEATURE:
        (A) NAME/KEY: CDS
        (B) LOCATION: 1..60

(xi) SEQUENCE DESCRIPTION: SEQ ID NO: 41:

CTGATCATCA CCGCTCTGTG GCGTGCTATT CCGATCCTGA TTATTATCGA ACGTATTATT     60

(2) INFORMATION FOR SEQ ID NO: 42:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA
```

(iii) HYPOTHETICAL: YES (ix) FEATURE:
            (A) NAME/KEY: CDS
            (B) LOCATION: 2..70

(xi) SEQUENCE DESCRIPTION: SEQ ID NO: 42:

AATTCTAGAT GATGCGCTCT ATGATGATAA GAATTGGGAT CGCGCGCCAC AACGCTGTTA        60

TTATCAACAT G        71

(2) INFORMATION FOR SEQ ID NO: 43:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: CDS
            (B) LOCATION: 2..70

(xi) SEQUENCE DESCRIPTION: SEQ ID NO: 43:

AATTCTAGTT CACAACCAAC TCGTTCTCCG TCGTCTCGCT CCGTCTGTTC CGGTTGTTCT        60

CCTTTTCCAT G        71

(2) INFORMATION FOR SEQ ID NO: 44:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: genomic DNA (iii) HYPOTHETICAL: YES (ix) FEATURE:
            (A) NAME/KEY: CDS
            (B) LOCATION: 3..71

(xi) SEQUENCE DESCRIPTION: SEQ ID NO: 44:

GATCCATGGA AAAGGAGAAC AACCGGAACA GACGGAGCGA GACGACGGAG AACGAGTTGG        60

TTGTGAACTA G        71

(2) INFORMATION FOR SEQ ID NO: 45:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..20

(xi) SEQUENCE DESCRIPTION: SEQ ID NO: 45:

Glu Lys Glu Asn Asn Arg Asn Arg Arg Ser Glu Thr Thr Glu Asn Glu
 1               5                  10                 15

Leu Val Val Asn

20

(2) INFORMATION FOR SEQ ID NO: 46:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: NO (ix) FEATURE:
        (A) NAME/KEY: CDS
        (B) LOCATION: 2..70

(xi) SEQUENCE DESCRIPTION: SEQ ID NO: 46:

AATTCTACTC GTTGTTGCTA CTCTCCGTTC TACTGTTCCG GTATTCGTTG TTGTTCAATC    60

TGTTGTTCAT G    71

(2) INFORMATION FOR SEQ ID NO: 47:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: YES (ix) FEATURE:
        (A) NAME/KEY: CDS
        (B) LOCATION: 3..71

(xi) SEQUENCE DESCRIPTION: SEQ ID NO: 47:

GATCCATGAA CAACAGATTG AACAACAACG AATACCGGAA CAGTAGAACG GAGAGTAGCA    60

ACAACGAGTA G    71

(2) INFORMATION FOR SEQ ID NO: 48:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 48:

Asn Asn Arg Leu Asn Asn Asn Glu Tyr Arg Asn Ser Arg Thr Glu
 1               5                  10                  15

Ser Ser Asn Asn Glu
            20